US008778981B2

(12) United States Patent
Kalayoglu et al.

(10) Patent No.: US 8,778,981 B2
(45) Date of Patent: Jul. 15, 2014

(54) METHODS AND COMPOSITIONS FOR LOCALLY INCREASING BODY FAT

(71) Applicant: Topokine Therapeutics, Inc., Newton, MA (US)

(72) Inventors: Murat V. Kalayoglu, Silver Spring, MD (US); Michael S. Singer, Newton Center, MA (US)

(73) Assignee: Topokine Therapeutics, Inc., Newton, MA (US)

( * ) Notice: Subject to any disclaimer, the term of this patent is extended or adjusted under 35 U.S.C. 154(b) by 0 days.

(21) Appl. No.: 14/086,785

(22) Filed: Nov. 21, 2013

(65) Prior Publication Data

US 2014/0142075 A1     May 22, 2014

Related U.S. Application Data

(60) Provisional application No. 61/729,051, filed on Nov. 21, 2012.

(51) Int. Cl.
| A61K 31/425 | (2006.01) |
| C07D 277/34 | (2006.01) |
| A61K 9/00 | (2006.01) |
| A61K 31/57 | (2006.01) |
| A61K 31/4439 | (2006.01) |

(52) U.S. Cl.
CPC .............. *A61K 9/0019* (2013.01); *A61K 31/57* (2013.01); *A61K 31/4439* (2013.01)
USPC ........... 514/369; 514/342; 514/256; 514/299; 514/367; 514/370; 548/183

(58) Field of Classification Search
USPC ................. 514/369, 342, 256, 299, 367, 370; 548/183
See application file for complete search history.

(56) References Cited

U.S. PATENT DOCUMENTS

| 4,270,537 A | 6/1981 | Romaine |
| 4,596,556 A | 6/1986 | Morrow et al. |

(Continued)

FOREIGN PATENT DOCUMENTS

| EA | 006556 B1 | 2/2006 |
| RU | 2 157 689 C2 | 10/2000 |

(Continued)

OTHER PUBLICATIONS

Kumar et al., Lecithin organogels as a potential phospholipid-structured system for topical drug delivery: a review. AAPS PharmSciTech. Oct. 6, 2005;6(2):E298-310.

(Continued)

*Primary Examiner* — Savitha Rao
(74) *Attorney, Agent, or Firm* — Wolf, Greenfield & Sacks, P.C.; C. Hunter Baker

(57) ABSTRACT

Provided are methods for increasing fat locally in a body of a subject in need thereof comprising percutaneously administering to the subcutaneous fat of the subject a thiazolidinedione or an orexigenic compound, or a pharmaceutically acceptable salt or prodrug thereof, optionally delivered as a composition comprising a pharmaceutically acceptable carrier, as described herein. In certain embodiments, the pharmaceutically acceptable carrier comprises a percutaneous carrier, as described herein. Further provided are compositions comprising a thiazolidinedione or an orexigenic compound, or a pharmaceutically acceptable salt or prodrug thereof, for use according to the invention.

20 Claims, 4 Drawing Sheets

(56) References Cited

U.S. PATENT DOCUMENTS

| | | | |
|---|---|---|---|
| 4,599,353 | A | 7/1986 | Bito |
| 4,790,824 | A | 12/1988 | Morrow et al. |
| 4,886,499 | A | 12/1989 | Cirelli et al. |
| 4,940,460 | A | 7/1990 | Casey et al. |
| 4,941,880 | A | 7/1990 | Burns |
| 5,011,062 | A | 4/1991 | Nakanishi et al. |
| 5,015,235 | A | 5/1991 | Crossman |
| 5,064,413 | A | 11/1991 | McKinnon et al. |
| 5,141,496 | A | 8/1992 | Dalto et al. |
| 5,190,521 | A | 3/1993 | Hubbard et al. |
| 5,296,504 | A | 3/1994 | Stjernschantz et al. |
| 5,312,335 | A | 5/1994 | McKinnon et al. |
| 5,328,483 | A | 7/1994 | Jacoby |
| 5,334,144 | A | 8/1994 | Alchas et al. |
| 5,339,163 | A | 8/1994 | Homma et al. |
| 5,383,851 | A | 1/1995 | McKinnon, Jr. et al. |
| 5,417,662 | A | 5/1995 | Hjertman et al. |
| 5,422,368 | A | 6/1995 | Stjernschantz et al. |
| 5,466,220 | A | 11/1995 | Brenneman |
| 5,480,381 | A | 1/1996 | Weston |
| 5,503,627 | A | 4/1996 | McKinnon et al. |
| 5,520,639 | A | 5/1996 | Peterson et al. |
| 5,527,288 | A | 6/1996 | Gross et al. |
| 5,569,189 | A | 10/1996 | Parsons |
| 5,599,302 | A | 2/1997 | Lilley et al. |
| 5,631,287 | A | 5/1997 | Schneider |
| 5,649,912 | A | 7/1997 | Peterson |
| 5,688,819 | A | 11/1997 | Woodward et al. |
| 5,704,911 | A | 1/1998 | Parsons |
| 5,849,792 | A | 12/1998 | Schneider |
| 5,886,035 | A | 3/1999 | Shirasawa et al. |
| 5,889,052 | A | 3/1999 | Klimko et al. |
| 5,893,397 | A | 4/1999 | Peterson et al. |
| 5,990,139 | A | 11/1999 | Yano et al. |
| 5,993,412 | A | 11/1999 | Deily et al. |
| 6,235,781 | B1 | 5/2001 | Weiner et al. |
| 6,262,105 | B1 | 7/2001 | Johnstone |
| 6,403,649 | B1 | 6/2002 | Woodward et al. |
| 6,646,001 | B2 | 11/2003 | Hellberg et al. |
| 6,730,707 | B2 | 5/2004 | Pintor et al. |
| 6,864,282 | B2 | 3/2005 | Ling et al. |
| 6,911,474 | B2 | 6/2005 | Piomelli et al. |
| 6,933,289 | B2 | 8/2005 | Lyons et al. |
| 7,070,768 | B2 | 7/2006 | Krauss |
| 7,125,542 | B2 | 10/2006 | Miller et al. |
| 7,351,404 | B2 | 4/2008 | Woodward et al. |
| 7,622,130 | B2 | 11/2009 | Kolodney et al. |
| 7,666,912 | B2 | 2/2010 | Grosskreutz et al. |
| 8,273,362 | B2 | 9/2012 | Philips et al. |
| 8,367,606 | B2 | 2/2013 | Tennenbaum et al. |
| 8,426,471 | B1 | 4/2013 | Kalayoglu et al. |
| 8,569,376 | B2 | 10/2013 | Kalayoglu et al. |
| 2003/0181354 | A1 | 9/2003 | Abdulrazik |
| 2004/0082660 | A1 | 4/2004 | Ueno |
| 2004/0115234 | A1 | 6/2004 | Gewirtz |
| 2005/0058614 | A1 | 3/2005 | Krauss |
| 2005/0261373 | A1 | 11/2005 | Ueno |
| 2008/0015257 | A1 | 1/2008 | Grosskreutz et al. |
| 2008/0107738 | A1 | 5/2008 | Philips et al. |
| 2009/0042909 | A1* | 2/2009 | Karnik .................. 514/256 |
| 2010/0234466 | A1 | 9/2010 | Grosskreutz et al. |
| 2012/0046256 | A1 | 2/2012 | Dobak |
| 2012/0295972 | A1 | 11/2012 | Woodward et al. |
| 2013/0178525 | A1 | 7/2013 | Kalayoglu et al. |

FOREIGN PATENT DOCUMENTS

| | | | |
|---|---|---|---|
| WO | WO 97/13537 | A1 | 4/1997 |
| WO | WO 97/37705 | A1 | 10/1997 |
| WO | WO 99/34850 | A1 | 7/1999 |
| WO | WO 03/066008 | A1 | 8/2003 |
| WO | WO 2005/034889 | A2 | 4/2005 |
| WO | WO 2005/034890 | A2 | 4/2005 |
| WO | WO 2007/111806 | A2 | 10/2007 |

OTHER PUBLICATIONS

Singh et al., Local deep tissue penetration of compounds after dermal application: structure-tissue penetration relationships. J Pharmacol Exp Ther. Nov. 1996;279(2):908-17.
Slama et al., Effect of pioglitazone on HIV-1-related lipodystrophy: a randomized double-blind placebo-controlled trial (ANRS 113). Antivir Ther. 2008;13(1):67-76.
Smith et al., Effect of pioglitazone on body composition and energy expenditure: a randomized controlled trial. Metabolism. Jan. 2005;54(1):24-32.
Invitation to Pay Additional Fees for PCT/US2007/005424, mailed Aug. 10, 2007.
International Search Report and Written Opinion for Application No. PCT/US2007/005424, published Nov. 26, 2007.
International Preliminary Report on Patentability for Application No. PCT/US2007/005424, mailed Oct. 2, 2008.
International Search Report and Written Opinion for Application No. PCT/US2012/070581, mailed May 30, 2013.
Baer et al., Measurement of body composition of live rats by electromagnetic conductance. Physiol Behav. Jun. 1993;53(6):1195-9.
Berge et al., Pharmaceutical salts. J Pharm Sci. Jan. 1977;66(1):1-19.
Bertin et al., Evaluation of dual-energy X-Ray absorptiometry for body-composition assessment in rats. J Nutr. Sep. 1998;128(9):1550-4.
Chapman et al., Glucocorticoid regulation of adipocyte differentiation: hormonal triggering of the developmental program and induction of a differentiation-dependent gene. J Cell Biol. Oct. 1985;101(4):1227-35.
Culebras et al., Total Body Water and the Exchangeable Hydrogen. II. Total body water and the exchangeable hydrogen. II. A review of comparative data from animals based on isotope dilution and desiccation, with a report of new data from the rat. Am J Physiol. Jan. 1977;232(1):R60-5.
Dahms et al., Correlation of percent body fat with body specific gravity in rats. J Nutr. Feb. 1982;112(2):398-400.
Ettmayer et al., Lessons learned from marketed and investigational prodrugs. J Med Chem. May 6, 2004;47(10):2393-404.
Gorin et al., Evidence for a role of protein kinase C in the stimulation of lipolysis by growth hormone and isoproterenol. Endocrinology. Jun. 1990;126(6):2973-82.
Gregoire et al., Understanding adipocyte differentiation. Physiol Rev. Jul. 1998;78(3):783-809.
Harris, F.D.A. to Restrict Avandia, Citing Heart Risk. The New York Times: Sep. 23, 2010. Accessed via nytreprints.com. 4 pages.
Künnecke et al., Quantitative body composition analysis in awake mice and rats by magnetic resonance relaxometry. Obes Res. Oct. 2004;12(10):1604-15.
Lesser et al., Modification of subcutaneous adipose tissue by a methylxanthine formulation: a double-blind controlled study. Dermatol Surg. Jun. 1999;25(6):455-62.
Löffler et al., Adipose tissue development: the role of precursor cells and adipogenic factors. Part II: The regulation of the adipogenic conversion by hormones and serum factors. Klin Wochenschr. Sep. 1, 1987;65(17):812-7.
Morissette et al., High-throughput crystallization: polymorphs, salts, co-crystals and solvates of pharmaceutical solids. Adv Drug Deliv Rev. Feb. 23, 2004;56(3):275-300.
Pantoja et al., Glucocorticoid signaling defines a novel commitment state during adipogenesis in vitro. Mol Biol Cell. Oct. 2008;19(10):4032-41. Epub Jul. 23, 2008.
Schiwek et al., Glucocorticoid hormones contribute to the adipogenic activity of human serum. Endocrinology. Feb. 1987;120(2):469-74. Abstract only.
Shi et al., A glucocorticoid-induced leucine-zipper protein, GILZ, inhibits adipogenesis of mesenchymal cells. EMBO Rep. Apr. 2003;4(4):374-80. Epub Mar. 14, 2003.
Shugart et al., Dexamethasone signaling is required to establish the postmitotic state of adipocyte development. Cell Growth Differ. Oct. 1997;8(10):1091-8.
Stella, Prodrugs as therapeutics. Expert Opin Ther Patents. 2004;14(3):277-80.

(56) References Cited

OTHER PUBLICATIONS

Testa, Prodrug research: futile or fertile? Biochem Pharmacol. Dec. 1, 2004;68(11):2097-106.
Vippagunta et al., Crystalline solids. Adv Drug Deliv Rev. May 16, 2001;48(1):3-26.
Wolff et al., Burger's Medicinal Chemistry and Drug Discovery. Fifth Edition. vol. I: Principles and Practice. 1994:975-7.
Chen et al., Simultaneous determination and pharmacokinetic study of metformin and rosiglitazone in human plasma by HPLC-ESI-MS. J Chromatogr Sci. Feb. 2011;49(2):94-100.
Damodharan et al., Skin Permeation of Rosiglitazone from Transdermal Matrix Patches. Pharmaceutical Technology. 2010;34(5):56-72.
Dayan et al., Delivery System Design in Topically Applied Formulations: An Overview. In: Delivery System Handbook for Personal Care and Cosmetic Products. Rosen, ed. William Andrew. 2005:103-104.
Domingo et al., Fat redistribution syndromes associated with HIV-1 infection and combination antiretroviral therapy. AIDS Rev. Apr.-Jun. 2012;14(2):112-23.
Ghosh et al., Feasibility of rosiglitazone maleate for transdermal delivery. Int J Pharma Res Innov. 2011;2:23-31.
Jacob et al., Weight gain in type 2 diabetes mellitus. Diabetes Obes Metab. May 2007;9(3):386-93.
Jonas et al., Drug Class Review: Newer diabetes medications, TZDs, and combinations. Final Original Report. Drug Effectiveness Review Project. Feb. 2011.
Kao, In Vitro Assessment of Dermal Absorption. In: Dermal and Ocular Toxicology: Fundamentals and Methods. Hobson, ed. CRC Press. 1991:267, 272-273.
Kayikcioglu et al., Semicircular lipoatrophy after intragluteal injection of benzathine penicillin. J Pediatr. Jul. 1996;129(1):166-7.
Kim et al., The increase in abdominal subcutaneous fat depot is an independent factor to determine the glycemic control after rosiglitazone treatment. Eur J Endocrinol. Aug. 2007;157(2):167-74.
Kuenzli et al., Effect of topical PPARbeta/delta and PPARgamma agonists on plaque psoriasis. A pilot study. Dermatology. 2003;206(3):252-6.
International Search Report and Written Opinion for PCT/US2013/071257, mailed Mar. 27, 2014.
Berenson et al., Changes in weight, total fat, percent body fat, and central-to-peripheral fat ratio associated with injectable and oral contraceptive use. *Am J Obstet Gynecol*. Mar. 2009; 200(3):329.e1-8.
Heim, Transdermal Administration of Anti-inflammatory Medications in Sports Injuries: Use of Iontophoresis and Phonophoresis to Enhance Delivery. *Int J Pharm Compd*. Jan.-Feb. 2006; 10(1):14-18.
Morley, Orexigenic and anabolic agents. Clin Geriatr Med. Nov. 2002; 18(4):853-66.
Wagstaff et al., Rosiglitazone: a review of its use in the management of type 2 diabetes mellitus. *Drugs*. 2002; 62(12)1805-37.
Zateyschikov, Thiazolidinediones and heart failure. Zhurnal Farmateka. 2005; 3(99):1-6. http://www.pharmateca.ru/ru/archive/article/5901 [last accessed Apr. 16, 2014].

\* cited by examiner

US 8,778,981 B2

METHODS AND COMPOSITIONS FOR LOCALLY INCREASING BODY FAT

RELATED APPLICATIONS

The present application claims priority under 35 U.S.C. §119(e) to U.S. provisional patent application, U.S. Ser. No. 61/729,051, filed Nov. 21, 2012, which is incorporated herein by reference.

FIELD OF THE INVENTION

The present invention relates to methods and compositions for increasing fat and/or adipocytes locally in the body of a subject. More specifically, body fat may be increased locally by percutaneously administering to the skin of a subject a compound that is a thiazolidinedione or an orexigenic pregnane derivative, optionally delivered as a composition comprising a pharmaceutically acceptable carrier, as described herein. In certain embodiments, the pharmaceutically acceptable carrier comprises a percutaneous carrier, as described herein.

BACKGROUND OF THE INVENTION

A number of medical and cosmetic conditions involve deficiencies of body fat. A body fat deficiency can be diffuse or concentrated on particular part(s) of the body, e.g., the head, face (e.g., cheeks, chin, jaw, lips), limbs (e.g., arms, hands, thighs, legs), and/or torso (e.g., chest, breast, abdomen, buttocks). A body fat deficiency can be due, for example, to loss of body fat (e.g., atrophy, lipoatrophy, wasting, degeneration, fibrosis, fat removal, trauma), failure of body fat to develop (e.g., aplasia, hypoplasia), and/or movement of fat away from a body part of interest (e.g., migration, descent, involution). Some causes of body fat deficiency include disease, metabolic state, medications, medical procedures, and trauma. Furthermore, a number of medical and cosmetic conditions can benefit from an increase in body fat even where a body fat deficiency does not exist. For example, skin wrinkles or loose skin can be ameliorated and/or treated by an increase of body fat underneath or near the skin wrinkles. Individuals dissatisfied with the appearance, size, or contour of body part(s), e.g., breast, buttocks, lips, face, and/or cheeks, can benefit from an increase in body fat in or near the body part(s).

A number of surgical methods have been developed to ameliorate and/or treat the above conditions. For example, adipose or other tissue can be extracted or liberated from one part of the body and redeposited in another (e.g., autologous fat transplantation). Likewise, tissue can be transplanted from a live human, cadaveric, or nonhuman donor. Space-occupying synthetic materials (e.g., silicone, saline, Restylane®, Juvederm®, Perlane®) can be deposited into or near a body part of interest. Generally, the above methods are invasive and can cause pain, scars, fibrosis, infection, inflammation, foreign body reaction, post-procedural deformity or regression, implant migration, and other adverse reactions.

Therefore, there is a need for new pharmaceutical compositions and methods for locally increasing fat in a body of a subject.

SUMMARY OF THE INVENTION

Given the disadvantages of surgery and injections, there has been a long felt need for a medicine that can be applied to the skin, penetrate the skin, and locally increase adipose tissue. U.S. Pat. No. 8,367,606 suggests, based on in vitro results, that an agonist of Peroxisome Proliferator-Activated Receptor Gamma (PPARγ), e.g., a thiazolidinedione, could be applied topically to the skin of an individual to increase body fat locally. However, this and other references lack working examples. In fact, in actual studies where such compounds have been administered to skin, no local increases in fat were noted. See, e.g., Kuenzli and Saurat, *Dermatology* (2003) 206:252-256.

Furthermore, the prior art fails to address or even recognize a key practical problem: how to deliver an effective amount of thiazolidinedione to subcutaneous fat without a systemic effect. This is crucial, because thiazolidinediones can have systemic toxicities such as obesity, cardiovascular disease, and increased incidence of certain cancers. Thus, systemic absorption must be minimized or avoided. Such delivery is technically challenging due to the "sink effect" of the dermal circulation, whereby drugs that penetrate the skin are rapidly absorbed into the systemic circulation by a dense network of dermal capillaries. For example, when the thiazolidinedione rosiglitazone is applied to the skin in a patch form, substantial amounts of the drug appear in the bloodstream, leading to systemic effects. See, e.g., Damodharan et al, Skin permeation of rosiglitazone from transdermal matrix patches, *Pharmaceutical Technology* (2010) 34:56-72. See also, e.g., Ghosh et al, Feasibility of rosiglitazone maleate for transdermal delivery, *Int. J. Pharm. Res. Innov.* (2011) 2:23-31.

The distinctions between superficial skin administration, systemic (transdermal) delivery to the bloodstream, and percutaneous delivery into fat are illustrated in FIG. 1. See, e.g., Dayan N, *Delivery System Design in Topically Applied Formulations: An Overview*, in Rosen M, *Delivery System Handbook for Personal Care and Cosmetic Products*, William Andrew, 2005, pp. 103-104; Kao J, *In Vitro Assessment of Dermal Absorption*, in Hobson D W, *Dermal and Ocular Toxicology: Fundamentals and Methods*, CRC Press, 1991, pp. 272-273. Delivering a drug across the skin and into the systemic circulation (e.g., transdermally, into the bloodstream) is a common practice. An example of such delivery is a nicotine patch, which results in delivery of nicotine across the skin into the bloodstream. Compared to transdermal administration, there are great technical challenges to delivering a drug across the skin and into subcutaneous fat while avoiding systemic exposure. See, e.g., Dayan et al, supra; Kao, supra. The reason for this is the "sink condition" of the dermal circulation. Because the dermis is invested by a network of capillaries with rapid blood flow, for any drug that penetrates the dermis, a wide concentration gradient is created between the skin and bloodstream. Thus, there is a strong tendency for drugs that penetrate into the dermis to diffuse rapidly down this gradient into the bloodstream. This sink phenomenon favors systemic delivery (e.g., to the bloodstream, as with a nicotine patch), but undermines attempts at local delivery (e.g., to subcutaneous fat, as in the present invention). No method of reasoning or prediction is available in the art to suggest which formulations, if any, can circumvent the sink condition.

The present invention arises from a discovery that percutaneously administering a thiazolidinedione or an orexigenic compound to a subject, i.e., such that a therapeutic effect is achieved in local subcutaneous fat without a systemic effect, effectively achieves a local increase in subcutaneous fat, e.g., without deleterious side effects.

Thus, in one aspect, provided is a method for increasing fat locally in a body of a subject in need thereof, the method comprising percutaneously delivering to the subcutaneous fat of the subject a thiazolidinedione or an orexigenic compound, or a pharmaceutically acceptable salt or prodrug thereof. In certain embodiments, the delivering (administering) step comprises topical application to the skin, or by intradermal injection, subcutaneous injection, intramuscular injection, intralesional injection, transmucosal injection, or mucosal application.

In certain embodiments, the increasing fat locally in a body of a subject results in an increase in subcutaneous fat thickness at the treated site on a subject (e.g., at least a 10%, at least a 20%, at least a 30%, or at least a 40% increase in subcutaneous fat thickness) compared to a control site on the subject, or compared to the baseline (pre-administration) subcutaneous fat measurement.

In certain embodiments, the subject suffers from a subcutaneous fat deficiency.

In certain embodiments, the subcutaneous fat deficiency is associated with a metabolic disorder. In certain embodiments, the metabolic disorder is insulin resistance, diabetes, lipase deficiency, wasting, malnutrition, paraneoplastic condition, anorexia, pernicious anemia, celiac disease, or malabsorption syndrome.

In certain embodiments, the subcutaneous fat deficiency is associated with an inflammatory condition. In certain embodiments, the inflammatory condition is complement component 3 (C3) deficiency, membranoproliferative glomerulonephritis, systemic lupus erythematosus, dermatomyositis, rheumatoid arthritis, temporal arteritis, or leukocytoclastic vasculitis.

In certain embodiments, the subcutaneous fat deficiency is acquired. In certain embodiments, the acquired subcutaneous fat deficiency is HIV-associated lipodystrophy, lipidema, acquired partial lipodystrophy, acquired generalized lipodystrophy, Parry-Romberg syndrome, juvenile dermatomyositis, centrifugal abdominal lipodystrophy, lipoatrophia annularis, or localized lipodystrophy.

In certain embodiments, the subcutaneous fat deficiency is congenital.

In certain embodiments, the congenital subcutaneous fat deficiency is congenital generalized lipodystrophy, familial partial dystrophy, Nakajo-Nishimura syndrome, Cockayne syndrome, SHORT syndrome, AREDYLD syndrome, mandibuloacral dysplasia, Keppen-Lubinsky syndrome, POEMS syndrome, Werner syndrome, Hutchinson-Gilford syndrome, or progeria.

In certain embodiments, the subcutaneous fat deficiency is caused by a lipoatrophy-causing mutation in a gene selected from the group consisting of APLD, AKT2, C3, CAV1, CGL1 (AGPAT2), and CGL2 (BSCL2), LMF1, LMNA, PLIN1, PPARG, PSMB8, PTRF, and ZMPSTE24.

In certain embodiments, the subcutaneous fat deficiency is caused by a medication, surgery, or an injury.

In certain embodiments, the subject suffers from wrinkles of the skin, and the method comprises minimizing the appearance of wrinkles.

In certain embodiments, the subject suffers from dissatisfaction with the size or contour of a body part, and the method comprises modifying the contour of the body part. In certain embodiments, the body part is the face, forehead, periorbital region of the face, midface, cheeks, chin, lips, other anterior structures from top of forehead to bottom of chin, breast, limbs, hands, trunk, hips, or buttocks.

In certain embodiments, the subject has transplanted fat, and the method comprises augmenting the transplanted fat.

In certain embodiments, the subject suffers from diabetes, HIV, familial lipodystrophy, or a subcutaneous fat deficiency.

In certain embodiments, the thiazolidinedione is a compound of Formula (I):

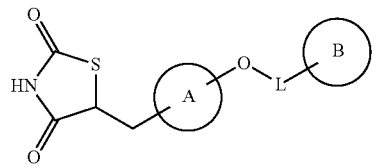

or a pharmaceutically acceptable salt or prodrug thereof; wherein:

Ring A is substituted or unsubstituted arylene or substituted or unsubstituted heteroarylene;

L is substituted or unsubstituted $C_{1-6}$ alkylene or substituted or unsubstituted hetero$C_{1-6}$alkylene; and Ring B is substituted or unsubstituted carbocyclyl, substituted or unsubstituted heterocyclyl, substituted or unsubstituted aryl, or substituted or unsubstituted heteroaryl.

In certain embodiments, the thiazolidinedione is selected from the group consisting of:

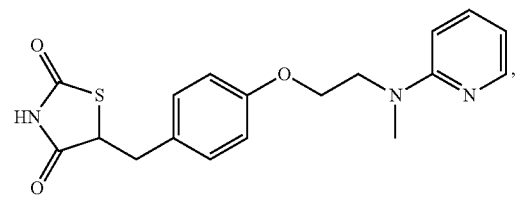

rosiglitazone

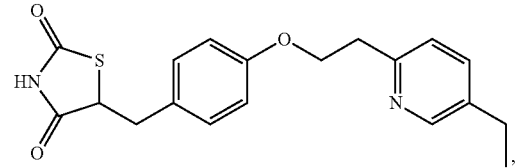

pioglitazone

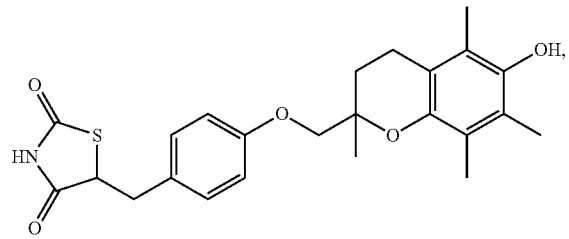

troglitazone

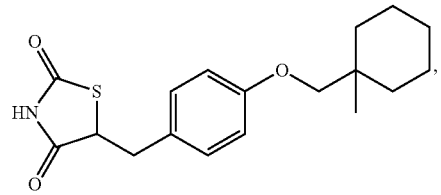

ciglitazone

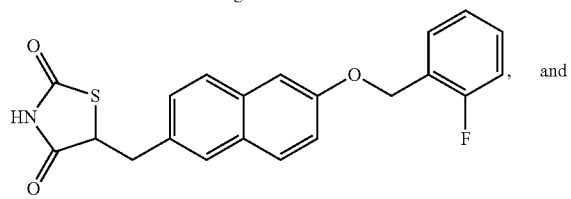

netoglitazone

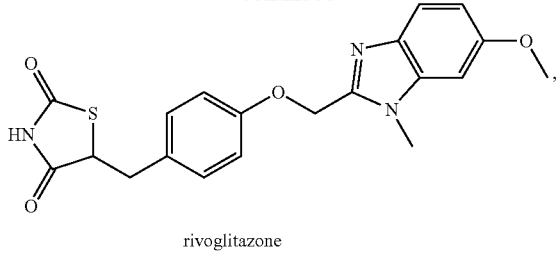

rivoglitazone and pharmaceutically acceptable salts and prodrugs thereof.

In certain embodiments, the orexigenic compound is a compound of Formula (II):

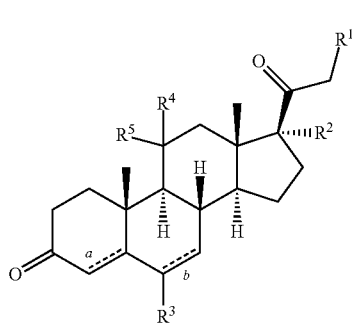

(II)

or a pharmaceutically acceptable salt or prodrug thereof; wherein:

each instance of ----- independently represents a single or double bond;

$R^1$ is hydrogen, hydroxyl, substituted hydroxyl, thiol, substituted thiol, amino, or substituted amino;

$R^2$ is hydrogen, hydroxyl, substituted hydroxyl, thiol, substituted thiol, amino, or substituted amino;

$R^3$ is hydrogen or substituted or unsubstituted $C_{1-6}$alkyl;

$R^4$ is hydrogen, hydroxyl, substituted hydroxyl, thiol, substituted thiol, amino, or substituted amino, and $R^5$ is hydrogen; or $R^4$ and $R^5$ are joined to form an oxo group =O.

In certain embodiments, the orexigenic compound is selected from the group consisting of:

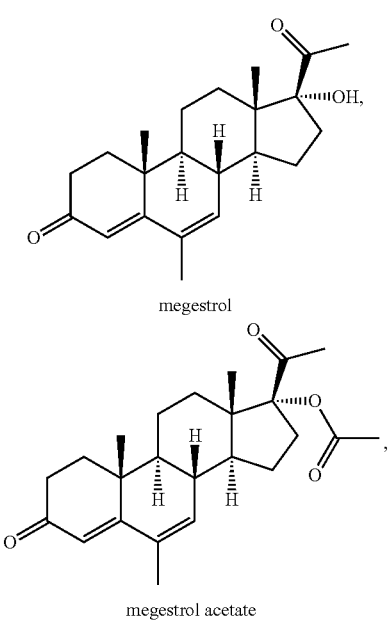

megestrol megestrol acetate

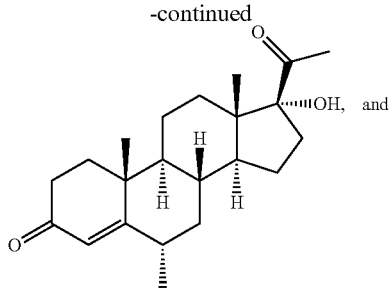

medroxyprogesterone

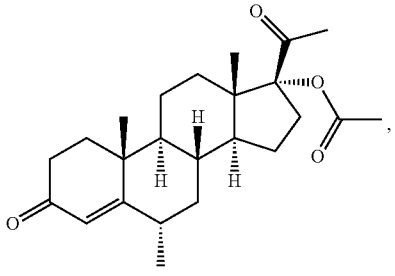

medroxyprogesterone acetate and pharmaceutically acceptable salts thereof.

In certain embodiments, the method comprises percutaneously delivering to the subcutaneous fat of the subject a composition comprising between about 0.0001 percent to about 5 percent by weight, inclusive, of the thiazolidinedione or an orexigenic compound, or pharmaceutically acceptable salt or prodrug thereof, to the subject. In certain embodiments, the concentration of the thiazolidinedione, or pharmaceutically acceptable salt or prodrug thereof, is between about 0.1 percent and about 5 percent by weight, inclusive. In certain embodiments, the concentration of the orexigenic compound, or pharmaceutically acceptable salt or prodrug thereof, is between about 0.1 percent and about 5 percent by weight, inclusive.

In another aspect, provided is a composition for percutaneous administration comprising a thiazolidinedione or an orexigenic compound, or a pharmaceutically acceptable salt or prodrug thereof, and a pharmaceutically acceptable carrier. In certain embodiments, the composition is a pharmaceutical composition or a cosmetic composition. In certain embodiments, the composition comprises a therapeutically effective amount of the thiazolidinedione or an orexigenic compound, or a pharmaceutically acceptable salt or prodrug thereof.

In certain embodiments, the pharmaceutically acceptable carrier comprises a percutaneous carrier. In certain embodiments, the composition comprises a percutaneous carrier. In certain embodiments, the composition comprises a carrier (optionally a percutaneous carrier) for intradermal injection, subcutaneous injection, intramuscular injection, intralesional injection, transmucosal injection, or mucosal application. In certain embodiments, the percutaneous carrier is a carrier according to one of the working examples provided herein; see, e.g., Examples 1 to 11.

In certain embodiments, the percutaneous carrier comprises one or more fatty acids. In certain embodiments, the fatty acid is oleic acid. In certain embodiments, the oleic acid is present at a concentration between about 1 and about 10 percent by weight.

In certain embodiments, the percutaneous carrier comprises one or more organic alcohols (e.g., ethanol and/or propylene glycol). In certain embodiments, the final concentration of the organic alcohol is between about 5 percent and about 99 percent by weight.

In certain embodiments, the composition comprises a thiazolidinedione or an orexigenic compound, or a pharmaceutically acceptable salt or prodrug thereof, and a percutaneous carrier comprising a fatty acid (e.g., oleic acid), wherein the fatty acid concentration is between about 1 and about 10 percent by weight in the composition. In certain embodiments, the percutaneous carrier further comprises an organic alcohol (e.g., propylene glycol and/or ethanol). In certain embodiments, the organic alcohol concentration is between about 5 percent and about 99 percent by weight in the composition. In certain embodiments, the composition further comprises a penetration enhancer. In certain embodiments, the composition further comprises a viscosity enhancing agent. In certain embodiments, the composition further comprises an antioxidant.

In certain embodiments, the composition is anhydrous (e.g., comprises between 0% to 1% water, inclusive).

In certain embodiment, the composition is a gel.

The details of one or more embodiments of the invention are set forth in the accompanying Figures below. Other features, objects, and advantages of the invention will be apparent from the Detailed Description, Examples, and the Claims.

DEFINITIONS

Definitions of specific functional groups and chemical terms are described in more detail below. The chemical elements are identified in accordance with the Periodic Table of the Elements, CAS version, Handbook of Chemistry and Physics, 75$^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3$^{rd}$ Edition, Cambridge University Press, Cambridge, 1987.

Compounds described herein can comprise one or more asymmetric centers, and thus can exist in various stereoisomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, E. L. *Stereochemistry of Carbon Compounds* (McGraw-Hill, NY, 1962); and Wilen, S. H. *Tables of Resolving Agents and Optical Resolutions* p. 268 (E. L. Eliel, Ed., Univ. of Notre Dame Press, Notre Dame, Ind. 1972). The invention additionally encompasses compounds as individual isomers substantially free of other isomers, and alternatively, as mixtures of various isomers.

When a range of values is listed, it is intended to encompass each value and sub-range within the range. For example "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

As used herein, "alkyl" refers to a radical of a straight-chain or branched saturated hydrocarbon group having from 1 to 10 carbon atoms ("$C_{1-10}$ alkyl"). In some embodiments, an alkyl group has 1 to 9 carbon atoms ("$C_{1-9}$alkyl"). In some embodiments, an alkyl group has 1 to 8 carbon atoms ("$C_{1-8}$ alkyl"). In some embodiments, an alkyl group has 1 to 7 carbon atoms ("$C_{1-7}$alkyl"). In some embodiments, an alkyl group has 1 to 6 carbon atoms ("$C_{1-6}$ alkyl"). In some embodiments, an alkyl group has 1 to 5 carbon atoms ("$C_{1-5}$alkyl"). In some embodiments, an alkyl group has 1 to 4 carbon atoms ("$C_{1-4}$alkyl"). In some embodiments, an alkyl group has 1 to 3 carbon atoms ("$C_{1-3}$alkyl"). In some embodiments, an alkyl group has 1 to 2 carbon atoms ("$C_{1-2}$alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), n-propyl ($C_3$), isopropyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), and n-hexyl ($C_6$). Additional examples of alkyl groups include n-heptyl ($C_7$), n-octyl ($C_8$) and the like. Unless otherwise specified, each instance of an alkyl group is independently unsubstituted (an "unsubstituted alkyl") or substituted (a "substituted alkyl") with one or more substituents. In certain embodiments, the alkyl group is an unsubstituted $C_{1-10}$ alkyl (e.g., —$CH_3$). In certain embodiments, the alkyl group is a substituted $C_{1-10}$ alkyl.

As used herein, "haloalkyl" is a substituted alkyl group as defined herein wherein one or more of the hydrogen atoms are independently replaced by a halogen, e.g., fluoro, bromo, chloro, or iodo. "Perhaloalkyl" is a subset of haloalkyl, and refers to an alkyl group wherein all of the hydrogen atoms are independently replaced by a halogen, e.g., fluoro, bromo, chloro, or iodo. In some embodiments, the haloalkyl moiety has 1 to 8 carbon atoms ("$C_{1-8}$ haloalkyl"). In some embodiments, the haloalkyl moiety has 1 to 6 carbon atoms ("$C_{1-6}$ haloalkyl"). In some embodiments, the haloalkyl moiety has 1 to 4 carbon atoms ("$C_{1-4}$ haloalkyl"). In some embodiments, the haloalkyl moiety has 1 to 3 carbon atoms ("$C_{1-3}$ haloalkyl"). In some embodiments, the haloalkyl moiety has 1 to 2 carbon atoms ("$C_{1-2}$ haloalkyl"). In some embodiments, all of the haloalkyl hydrogen atoms are replaced with fluoro to provide a perfluoroalkyl group. In some embodiments, all of the haloalkyl hydrogen atoms are replaced with chloro to provide a "perchloroalkyl" group. Examples of haloalkyl groups include —$CF_3$, —$CF_2CF_3$, —$CF_2CF_2CF_3$, —$CCl_3$, —$CFCl_2$, —$CF_2Cl$, and the like.

As used herein, "heteroalkyl" refers to an alkyl group as defined herein which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkyl group refers to a saturated group having from 1 to 10 carbon atoms and 1 or more heteroatoms within the parent chain ("hetero$C_{1-10}$ alkyl"). In some embodiments, a heteroalkyl group is a saturated group having 1 to 9 carbon atoms and 1 or more heteroatoms within the parent chain ("hetero$C_{1-9}$ alkyl"). In some embodiments, a heteroalkyl group is a saturated group having 1 to 8 carbon atoms and 1 or more heteroatoms within the parent chain ("hetero$C_{1-8}$ alkyl"). In some embodiments, a heteroalkyl group is a saturated group having 1 to 7 carbon atoms and 1 or more heteroatoms within the parent chain ("hetero$C_{1-7}$ alkyl"). In some embodiments, a heteroalkyl group is a saturated group having 1 to 6 carbon atoms and 1 or more heteroatoms within the parent chain ("heteroC$_{1-6}$ alkyl"). In some embodiments, a heteroalkyl group is a saturated group having 1 to 5 carbon atoms and 1 or 2 heteroatoms within the parent chain ("heteroC$_{1-5}$ alkyl"). In some embodiments, a heteroalkyl group is a saturated group having 1 to 4 carbon atoms and 1 or 2 heteroatoms within the parent chain ("heteroC$_{1-4}$alkyl"). In some embodiments, a heteroalkyl group is a saturated group having 1 to 3 carbon atoms and 1 heteroatom within the parent chain ("heteroC$_{1-3}$ alkyl"). In some embodiments, a heteroalkyl group is a saturated group having 1 to 2 carbon atoms and 1 heteroatom within the parent chain ("heteroC$_{1-2}$ alkyl"). In some embodiments, a heteroalkyl group is a saturated group having 1 carbon atom and 1 heteroatom ("heteroC$_1$ alkyl"). In some embodiments, a heteroalkyl group is a saturated group having 2 to 6 carbon atoms and 1 or 2 heteroatoms within the parent chain ("heteroC$_{2-6}$ alkyl"). Unless otherwise specified, each instance of a heteroalkyl group is independently unsubstituted (an "unsubstituted heteroalkyl") or substituted (a "substituted heteroalkyl") with one or more substituents. In certain embodiments, the heteroalkyl group is an unsubstituted heteroC$_{1-10}$ alkyl. In certain embodiments, the heteroalkyl group is a substituted heteroC$_{1-10}$ alkyl.

As used herein, "alkenyl" refers to a radical of a straight-chain or branched hydrocarbon group having from 2 to 10 carbon atoms and one or more carbon-carbon double bonds (e.g., 1, 2, 3, or 4 double bonds). In some embodiments, an alkenyl group has 2 to 9 carbon atoms ("C$_{2-9}$ alkenyl"). In some embodiments, an alkenyl group has 2 to 8 carbon atoms ("C$_{2-8}$ alkenyl"). In some embodiments, an alkenyl group has 2 to 7 carbon atoms ("C$_{2-7}$ alkenyl"). In some embodiments, an alkenyl group has 2 to 6 carbon atoms ("C$_{2-6}$ alkenyl"). In some embodiments, an alkenyl group has 2 to 5 carbon atoms ("C$_{2-5}$alkenyl"). In some embodiments, an alkenyl group has 2 to 4 carbon atoms ("C$_{2-4}$ alkenyl"). In some embodiments, an alkenyl group has 2 to 3 carbon atoms ("C$_{2-3}$ alkenyl"). In some embodiments, an alkenyl group has 2 carbon atoms ("C$_2$ alkenyl"). The one or more carbon-carbon double bonds can be internal (such as in 2-butenyl) or terminal (such as in 1-butenyl). Examples of C$_{2-4}$ alkenyl groups include ethenyl (C$_2$), 1-propenyl (C$_3$), 2-propenyl (C$_3$), 1-butenyl (C$_4$), 2-butenyl (C$_4$), butadienyl (C$_4$), and the like. Examples of C$_{2-6}$ alkenyl groups include the aforementioned C$_{2-4}$ alkenyl groups as well as pentenyl (C$_5$), pentadienyl (C$_5$), hexenyl (C$_6$), and the like. Additional examples of alkenyl include heptenyl (C$_7$), octenyl (C$_8$), octatrienyl (C$_8$), and the like. Unless otherwise specified, each instance of an alkenyl group is independently unsubstituted (an "unsubstituted alkenyl") or substituted (a "substituted alkenyl") with one or more substituents. In certain embodiments, the alkenyl group is an unsubstituted C$_{2-10}$ alkenyl. In certain embodiments, the alkenyl group is a substituted C$_{2-10}$ alkenyl.

As used herein, "heteroalkenyl" refers to an alkenyl group as defined herein which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkenyl group refers to a group having from 2 to 10 carbon atoms, at least one double bond, and 1 or more heteroatoms within the parent chain ("heteroC$_{2-10}$ alkenyl"). In some embodiments, a heteroalkenyl group has 2 to 9 carbon atoms at least one double bond, and 1 or more heteroatoms within the parent chain ("heteroC$_{2-9}$ alkenyl"). In some embodiments, a heteroalkenyl group has 2 to 8 carbon atoms, at least one double bond, and 1 or more heteroatoms within the parent chain ("heteroC$_{2-8}$ alkenyl"). In some embodiments, a heteroalkenyl group has 2 to 7 carbon atoms, at least one double bond, and 1 or more heteroatoms within the parent chain ("heteroC$_{2-7}$ alkenyl"). In some embodiments, a heteroalkenyl group has 2 to 6 carbon atoms, at least one double bond, and 1 or more heteroatoms within the parent chain ("heteroC$_{2-6}$ alkenyl"). In some embodiments, a heteroalkenyl group has 2 to 5 carbon atoms, at least one double bond, and 1 or 2 heteroatoms within the parent chain ("heteroC$_{2-5}$ alkenyl"). In some embodiments, a heteroalkenyl group has 2 to 4 carbon atoms, at least one double bond, and 1 or 2 heteroatoms within the parent chain ("heteroC$_{2-4}$ alkenyl"). In some embodiments, a heteroalkenyl group has 2 to 3 carbon atoms, at least one double bond, and 1 heteroatom within the parent chain ("heteroC$_{2-3}$ alkenyl"). In some embodiments, a heteroalkenyl group has 2 to 6 carbon atoms, at least one double bond, and 1 or 2 heteroatoms within the parent chain ("heteroC$_{2-6}$ alkenyl"). Unless otherwise specified, each instance of a heteroalkenyl group is independently unsubstituted (an "unsubstituted heteroalkenyl") or substituted (a "substituted heteroalkenyl") with one or more substituents. In certain embodiments, the heteroalkenyl group is an unsubstituted heteroC$_{2-10}$ alkenyl. In certain embodiments, the heteroalkenyl group is a substituted heteroC$_{2-10}$ alkenyl.

As used herein, "alkynyl" refers to a radical of a straight-chain or branched hydrocarbon group having from 2 to 10 carbon atoms and one or more carbon-carbon triple bonds (e.g., 1, 2, 3, or 4 triple bonds) ("C$_{2-10}$ alkynyl"). In some embodiments, an alkynyl group has 2 to 9 carbon atoms ("C$_{2-9}$ alkynyl"). In some embodiments, an alkynyl group has 2 to 8 carbon atoms ("C$_{2-8}$ alkynyl"). In some embodiments, an alkynyl group has 2 to 7 carbon atoms ("C$_{2-7}$ alkynyl"). In some embodiments, an alkynyl group has 2 to 6 carbon atoms ("C$_{2-6}$ alkynyl"). In some embodiments, an alkynyl group has 2 to 5 carbon atoms ("C$_{2-5}$ alkynyl"). In some embodiments, an alkynyl group has 2 to 4 carbon atoms ("C$_{2-4}$ alkynyl"). In some embodiments, an alkynyl group has 2 to 3 carbon atoms ("C$_{2-3}$ alkynyl"). In some embodiments, an alkynyl group has 2 carbon atoms ("C$_2$ alkynyl"). The one or more carbon-carbon triple bonds can be internal (such as in 2-butynyl) or terminal (such as in 1-butynyl). Examples of C$_{2-4}$ alkynyl groups include, without limitation, ethynyl (C$_2$), 1-propynyl (C$_3$), 2-propynyl (C$_3$), 1-butynyl (C$_4$), 2-butynyl (C$_4$), and the like. Examples of C$_{2-6}$ alkenyl groups include the aforementioned C$_{2-4}$ alkynyl groups as well as pentynyl (C$_5$), hexynyl (C$_6$), and the like. Additional examples of alkynyl include heptynyl (C$_7$), octynyl (C$_8$), and the like. Unless otherwise specified, each instance of an alkynyl group is independently unsubstituted (an "unsubstituted alkynyl") or substituted (a "substituted alkynyl") with one or more substituents. In certain embodiments, the alkynyl group is an unsubstituted C$_{2-10}$ alkynyl. In certain embodiments, the alkynyl group is a substituted C$_{2-10}$ alkynyl.

As used herein, "heteroalkynyl" refers to an alkynyl group as defined herein which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkynyl group refers to a group having from 2 to 10 carbon atoms, at least one triple bond, and 1 or more heteroatoms within the parent chain ("heteroC$_{2-10}$ alkynyl"). In some embodiments, a heteroalkynyl group has 2 to 9 carbon atoms, at least one triple bond, and 1 or more heteroatoms within the parent chain ("heteroC$_{2-9}$ alkynyl"). In some embodiments, a heteroalkynyl group has 2 to 8 carbon atoms, at least one triple bond, and 1 or more heteroatoms within the parent chain ("heteroC$_{2-8}$ alkynyl"). In some embodiments, a heteroalkynyl group has 2 to 7 carbon atoms, at least one triple bond, and 1 or more heteroatoms within the parent chain ("heteroC$_{2-7}$ alkynyl"). In some embodiments, a heteroalkynyl group has 2 to 6 carbon atoms, at least one triple bond, and 1 or more heteroatoms within the parent chain ("heteroC$_{2-6}$ alkynyl"). In some embodiments, a heteroalkynyl group has 2 to 5 carbon atoms, at least one triple bond, and 1 or 2 heteroatoms within the parent chain ("heteroC$_{2-5}$ alkynyl"). In some embodiments, a heteroalkynyl group has 2 to 4 carbon atoms, at least one triple bond, and 1 or 2 heteroatoms within the parent chain ("heteroC$_{2-4}$ alkynyl"). In some embodiments, a heteroalkynyl group has 2 to 3 carbon atoms, at least one triple bond, and 1 heteroatom within the parent chain ("heteroC$_{2-3}$ alkynyl"). In some embodiments, a heteroalkynyl group has 2 to 6 carbon atoms, at least one triple bond, and 1 or 2 heteroatoms within the parent chain ("heteroC$_{2-6}$ alkynyl"). Unless otherwise specified, each instance of a heteroalkynyl group is independently unsubstituted (an "unsubstituted heteroalkynyl") or substituted (a "substituted heteroalkynyl") with one or more substituents. In certain embodiments, the heteroalkynyl group is an unsubstituted heteroC$_{2-10}$ alkynyl. In certain embodiments, the heteroalkynyl group is a substituted heteroC$_{2-10}$ alkynyl.

As used herein, "carbocyclyl" or "carbocyclic" refers to a radical of a non-aromatic cyclic hydrocarbon group having from 3 to 10 ring carbon atoms ("C$_{30-10}$ carbocyclyl") and zero heteroatoms in the non-aromatic ring system. In some embodiments, a carbocyclyl group has 3 to 8 ring carbon atoms ("C$_{3-8}$ carbocyclyl"). In some embodiments, a carbocyclyl group has 3 to 7 ring carbon atoms ("C$_{3-7}$ carbocyclyl"). In some embodiments, a carbocyclyl group has 3 to 6 ring carbon atoms ("C$_{3-6}$ carbocyclyl"). In some embodiments, a carbocyclyl group has 4 to 6 ring carbon atoms ("C$_{4-6}$ carbocyclyl"). In some embodiments, a carbocyclyl group has 5 to 6 ring carbon atoms ("C$_{5-6}$ carbocyclyl"). In some embodiments, a carbocyclyl group has 5 to 10 ring carbon atoms ("C$_{5-10}$ carbocyclyl"). Exemplary C$_{3-6}$ carbocyclyl groups include, without limitation, cyclopropyl (C$_3$), cyclopropenyl (C$_3$), cyclobutyl (C$_4$), cyclobutenyl (C$_4$), cyclopentyl (C$_5$), cyclopentenyl (C$_5$), cyclohexyl (C$_6$), cyclohexenyl (C$_6$), cyclohexadienyl (C$_6$), and the like. Exemplary C$_{3-8}$ carbocyclyl groups include, without limitation, the aforementioned C$_{3-6}$ carbocyclyl groups as well as cycloheptyl (C$_7$), cycloheptenyl (C$_7$), cycloheptadienyl (C$_7$), cycloheptatrienyl (C$_7$), cyclooctyl (C$_8$), cyclooctenyl (C$_8$), bicyclo[2.2.1]heptanyl (C$_7$), bicyclo[2.2.2]octanyl (C$_8$), and the like. Exemplary C$_{3-10}$ carbocyclyl groups include, without limitation, the aforementioned C$_{3-8}$ carbocyclyl groups as well as cyclononyl (C$_9$), cyclononenyl (C$_9$), cyclodecyl (C$_{10}$), cyclodecenyl (C$_{10}$), octahydro-1H-indenyl (C$_9$), decahydronaphthalenyl (C$_{10}$), spiro[4.5]decanyl (C$_{10}$), and the like. As the foregoing examples illustrate, in certain embodiments, the carbocyclyl group is either monocyclic ("monocyclic carbocyclyl") or polycyclic (e.g., containing a fused, bridged or spiro ring system such as a bicyclic system ("bicyclic carbocyclyl") or tricyclic system ("tricyclic carbocyclyl")) and can be saturated or can contain one or more carbon-carbon double or triple bonds. "Carbocyclyl" also includes ring systems wherein the carbocyclyl ring, as defined above, is fused with one or more aryl or heteroaryl groups wherein the point of attachment is on the carbocyclyl ring, and in such instances, the number of carbons continue to designate the number of carbons in the carbocyclic ring system. Unless otherwise specified, each instance of a carbocyclyl group is independently unsubstituted (an "unsubstituted carbocyclyl") or substituted (a "substituted carbocyclyl") with one or more substituents. In certain embodiments, the carbocyclyl group is an unsubstituted C$_{3-10}$ carbocyclyl. In certain embodiments, the carbocyclyl group is a substituted C$_{3-10}$ carbocyclyl.

In some embodiments, "carbocyclyl" is a monocyclic, saturated carbocyclyl group having from 3 to 10 ring carbon atoms ("C$_{3-10}$ cycloalkyl"). In some embodiments, a cycloalkyl group has 3 to 8 ring carbon atoms ("C$_{3-8}$ cycloalkyl"). In some embodiments, a cycloalkyl group has 3 to 6 ring carbon atoms ("C$_{3-6}$ cycloalkyl"). In some embodiments, a cycloalkyl group has 4 to 6 ring carbon atoms ("C$_{4-6}$ cycloalkyl"). In some embodiments, a cycloalkyl group has 5 to 6 ring carbon atoms ("C$_{5-6}$ cycloalkyl"). In some embodiments, a cycloalkyl group has 5 to 10 ring carbon atoms ("C$_{5-10}$ cycloalkyl"). Examples of C$_{5-6}$ cycloalkyl groups include cyclopentyl (C$_5$) and cyclohexyl (C$_5$). Examples of C$_{3-6}$ cycloalkyl groups include the aforementioned C$_{5-6}$ cycloalkyl groups as well as cyclopropyl (C$_3$) and cyclobutyl (C$_4$). Examples of C$_{3-8}$ cycloalkyl groups include the aforementioned C$_{3-6}$ cycloalkyl groups as well as cycloheptyl (C$_7$) and cyclooctyl (C$_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is an unsubstituted C$_{3-10}$ cycloalkyl. In certain embodiments, the cycloalkyl group is a substituted C$_{3-10}$ cycloalkyl.

As used herein, "heterocyclyl" or "heterocyclic" refers to a radical of a 3- to 14-membered non-aromatic ring system having ring carbon atoms and 1 to 4 ring heteroatoms, wherein each heteroatom is independently selected from nitrogen, oxygen, and sulfur ("3-14 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or polycyclic (e.g., a fused, bridged or spiro ring system such as a bicyclic system ("bicyclic heterocyclyl") or tricyclic system ("tricyclic heterocyclyl")), and can be saturated or can contain one or more carbon-carbon double or triple bonds. Heterocyclyl polycyclic ring systems can include one or more heteroatoms in one or both rings. "Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. Unless otherwise specified, each instance of heterocyclyl is independently unsubstituted (an "unsubstituted heterocyclyl") or substituted (a "substituted heterocyclyl") with one or more substituents. In certain embodiments, the heterocyclyl group is an unsubstituted 3-14 membered heterocyclyl. In certain embodiments, the heterocyclyl group is a substituted 3-14 membered heterocyclyl.

In some embodiments, a heterocyclyl group is a 5-10 membered non-aromatic ring system having ring carbon atoms and 1-4 ring heteroatoms, wherein each heteroatom is independently selected from nitrogen, oxygen, and sulfur ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has 1 ring heteroatom selected from nitrogen, oxygen, and sulfur.

Exemplary 3-membered heterocyclyl groups containing 1 heteroatom include, without limitation, azirdinyl, oxiranyl, thiorenyl. Exemplary 4-membered heterocyclyl groups containing 1 heteroatom include, without limitation, azetidinyl, oxetanyl and thietanyl. Exemplary 5-membered heterocyclyl groups containing 1 heteroatom include, without limitation, tetrahydrofuranyl, dihydrofuranyl, tetrahydrothiophenyl, dihydrothiophenyl, pyrrolidinyl, dihydropyrrolyl and pyrrolyl-2,5-dione. Exemplary 5-membered heterocyclyl groups containing 2 heteroatoms include, without limitation, dioxolanyl, oxathiolanyl and dithiolanyl. Exemplary 5-membered heterocyclyl groups containing 3 heteroatoms include, without limitation, triazolinyl, oxadiazolinyl, and thiadiazolinyl. Exemplary 6-membered heterocyclyl groups containing 1 heteroatom include, without limitation, piperidinyl, tetrahydropyranyl, dihydropyranyl, dihydropyridinyl, and thianyl. Exemplary 6-membered heterocyclyl groups containing 2 heteroatoms include, without limitation, piperazinyl, morpholinyl, dithianyl, dioxanyl. Exemplary 6-membered heterocyclyl groups containing 2 heteroatoms include, without limitation, triazinanyl. Exemplary 7-membered heterocyclyl groups containing 1 heteroatom include, without limitation, azepanyl, oxepanyl and thiepanyl. Exemplary 8-membered heterocyclyl groups containing 1 heteroatom include, without limitation, azocanyl, oxecanyl and thiocanyl. Exemplary bicyclic heterocyclyl groups include, without limitation, indolinyl, isoindolinyl, dihydrobenzofuranyl, dihydrobenzothienyl, tetra-hydrobenzothienyl, tetrahydrobenzofuranyl, tetrahydroindolyl, tetrahydroquinolinyl, tetrahydroisoquinolinyl, decahydroquinolinyl, decahydroisoquinolinyl, octahydrochromenyl, octahydroisochromenyl, decahydronaphthyridinyl, decahydro-1,8-naphthyridinyl, octahydropyrrolo[3,2-b]pyrrole, indolinyl, phthalimidyl, naphthalimidyl, chromanyl, chromenyl, 1H-benzo[e][1,4]diazepinyl, 1,4,5,7-tetrahydropyrano[3,4-b]pyrrolyl, 5,6-dihydro-4H-furo[3,2-b]pyrrolyl, 6,7-dihydro-5H-furo[3,2-b]pyranyl, 5,7-dihydro-4H-thieno[2,3-c]pyranyl, 2,3-dihydro-1H-pyrrolo[2,3-b]pyridinyl, 2,3-dihydrofuro[2,3-b]pyridinyl, 4,5,6,7-tetrahydro-1H-pyrrolo[2,3-b]pyridinyl, 4,5,6,7-tetrahydrofuro[3,2-c]pyridinyl, 4,5,6,7-tetrahydrothieno[3,2-b]pyridinyl, 1,2,3,4-tetrahydro-1,6-naphthyridinyl, and the like.

As used herein, "aryl" refers to a radical of a monocyclic or polycyclic (e.g., bicyclic or tricyclic) 4n+2 aromatic ring system (e.g., having 6, 10, or 14 π electrons shared in a cyclic array) having 6-14 ring carbon atoms and zero heteroatoms provided in the aromatic ring system ("$C_{6-14}$ aryl"). In some embodiments, an aryl group has 6 ring carbon atoms ("$C_6$ aryl"; e.g., phenyl). In some embodiments, an aryl group has 10 ring carbon atoms ("$C_{10}$ aryl"; e.g., naphthyl such as 1-naphthyl and 2-naphthyl). In some embodiments, an aryl group has 14 ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently unsubstituted (an "unsubstituted aryl") or substituted (a "substituted aryl") with one or more substituents. In certain embodiments, the aryl group is an unsubstituted $C_{6-14}$ aryl. In certain embodiments, the aryl group is a substituted $C_{6-14}$ aryl.

As used herein, "heteroaryl" refers to a radical of a 5-14 membered monocyclic or polycyclic (e.g., bicyclic, tricyclic) 4n+2 aromatic ring system (e.g., having 6, 10, or 14 π electrons shared in a cyclic array) having ring carbon atoms and 1-4 ring heteroatoms provided in the aromatic ring system, wherein each heteroatom is independently selected from nitrogen, oxygen and sulfur ("5-14 membered heteroaryl"). In heteroaryl groups that contain one or more nitrogen atoms, the point of attachment can be a carbon or nitrogen atom, as valency permits. Heteroaryl polycyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused polycyclic (aryl/heteroaryl) ring system. Polycyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently unsubstituted (an "unsubstituted heteroaryl") or substituted (a "substituted heteroaryl") with one or more substituents. In certain embodiments, the heteroaryl group is an unsubstituted 5-14 membered heteroaryl. In certain embodiments, the heteroaryl group is a substituted 5-14 membered heteroaryl.

Exemplary 5-membered heteroaryl groups containing 1 heteroatom include, without limitation, pyrrolyl, furanyl and thiophenyl. Exemplary 5-membered heteroaryl groups containing 2 heteroatoms include, without limitation, imidazolyl, pyrazolyl, oxazolyl, isoxazolyl, thiazolyl, and isothiazolyl. Exemplary 5-membered heteroaryl groups containing 3 heteroatoms include, without limitation, triazolyl, oxadiazolyl, and thiadiazolyl. Exemplary 5-membered heteroaryl groups containing 4 heteroatoms include, without limitation, tetrazolyl. Exemplary 6-membered heteroaryl groups containing 1 heteroatom include, without limitation, pyridinyl. Exemplary 6-membered heteroaryl groups containing 2 heteroatoms include, without limitation, pyridazinyl, pyrimidinyl, and pyrazinyl. Exemplary 6-membered heteroaryl groups containing 3 or 4 heteroatoms include, without limitation, triazinyl and tetrazinyl, respectively. Exemplary 7-membered heteroaryl groups containing 1 heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl. Exemplary tricyclic heteroaryl groups include, without limitation, phenanthridinyl, dibenzofuranyl, carbazolyl, acridinyl, phenothiazinyl, phenoxazinyl and phenazinyl.

As used herein, the term "partially unsaturated" refers to a ring moiety that includes at least one double or triple bond. The term "partially unsaturated" is intended to encompass rings having multiple sites of unsaturation, but is not intended to include aromatic groups (e.g., aryl or heteroaryl moieties) as herein defined.

As used herein, the term "saturated" refers to a ring moiety that does not contain a double or triple bond, i.e., the ring contains all single bonds.

Affixing the suffix "-ene" to a group indicates the group is a divalent moiety, e.g., alkylene is the divalent moiety of alkyl, alkenylene is the divalent moiety of alkenyl, alkynylene is the divalent moiety of alkynyl, heteroalkylene is the divalent moiety of heteroalkyl, heteroalkenylene is the divalent moiety of heteroalkenyl, heteroalkynylene is the divalent moiety of heteroalkynyl, carbocyclylene is the divalent moiety of carbocyclyl, heterocyclylene is the divalent moiety of heterocyclyl, arylene is the divalent moiety of aryl, and heteroarylene is the divalent moiety of heteroaryl.

As understood from the above, alkyl, alkenyl, alkynyl, heteroalkyl, heteroalkenyl, heteroalkynyl, carbocyclyl, heterocyclyl, aryl, and heteroaryl groups, as defined herein, are, in certain embodiments, optionally substituted. Optionally substituted refers to a group which may be substituted or unsubstituted (e.g., "substituted" or "unsubstituted" alkyl, "substituted" or "unsubstituted" alkenyl, "substituted" or "unsubstituted" alkynyl, "substituted" or "unsubstituted" heteroalkyl, "substituted" or "unsubstituted" heteroalkenyl, "substituted" or "unsubstituted" heteroalkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted" means that at least one hydrogen present on a group is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, any of the substituents described herein that results in the formation of a stable compound. The present invention contemplates any and all such combinations in order to arrive at a stable compound. For purposes of this invention, heteroatoms such as nitrogen may have hydrogen substituents and/or any suitable substituent as described herein which satisfy the valencies of the heteroatoms and results in the formation of a stable moiety.

Exemplary carbon atom substituents include, but are not limited to, halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3^+$X$^-$, —N(OR$^{cc}$)R$^{bb}$, —SH, —SR$^{aa}$, —SSR$^{cc}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$—C(=S)N(R$^{bb}$)$_2$, —C(=O)SR$^{aa}$, —C(=S)SR$^{aa}$, —SC(=S)SR$^{aa}$, —SC(=O)SR$^{aa}$, —OC(=O)SR$^{aa}$, —SC(=O)OR$^{aa}$, —SC(=O)R$^{aa}$, —P(=O)$_2$R$^{aa}$, —OP(=O)$_2$R$^{aa}$, —P(=O)(R$^{aa}$)$_2$, —OP(=O)(R$^{aa}$)$_2$, —OP(=O)(OR$^{cc}$)$_2$, —P(=O)$_2$N(R$^{bb}$)$_2$, —OP(=O)$_2$N(R$^{bb}$)$_2$, —P(=O)(NR$^{bb}$)$_2$, —OP(=O)(NR$^{bb}$)$_2$, —NR$^{bb}$P(=O)(OR$^{cc}$)$_2$, —NR$^{bb}$P(=O)(NR$^{bb}$)$_2$, —P(R$^{cc}$)$_2$, —P(R$^{cc}$)$_3$, —OP(R$^{cc}$)$_2$, —OP(R$^{cc}$)$_3$, —B(R$^{aa}$)$_2$, —B(OR$^{cc}$)$_2$, —BR$^{aa}$(OR$^{cc}$), C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$ alkenyl, heteroC$_{2-10}$alkynyl, C$_{3-14}$ carbocyclyl, 3-14 membered heterocyclyl, C$_{6-4}$ aryl, and 5-14 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

or two geminal hydrogens on a carbon atom are replaced with the group =O, =S, =NN(R$^{bb}$)$_2$, =NNR$^{bb}$C(=O)R$^{aa}$, =NNR$^{bb}$C(=O)OR$^{aa}$, =NNR$^{bb}$S(=O)$_2$R$^{aa}$, =NR$^{bb}$, or =NOR$^{cc}$;

each instance of R$^{aa}$ is, independently, selected from C$_{1-10}$ alkyl, C$_{1-10}$ perhaloalkyl, C$_{2-10}$ alkenyl, C$_{2-10}$ alkynyl, heteroC$_{1-10}$alkyl, heteroC$_{2-10}$ alkenyl, heteroC$_{2-10}$alkynyl, C$_{3-10}$ carbocyclyl, 3-14 membered heterocyclyl, C$_{6-14}$ aryl, and 5-14 membered heteroaryl, or two R$^{aa}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

each instance of R$^{bb}$ is, independently, selected from hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, P(=O)$_2$R$^{aa}$, —P(=O)(R$^{aa}$)$_2$, —P(=O)$_2$N(R$^{cc}$)$_2$, —P(=O)(NR$^{cc}$)$_2$, C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$ alkenyl, heteroC$_{2-10}$alkynyl, C$_{3-10}$ carbocyclyl, 3-14 membered heterocyclyl, C$_{6-14}$ aryl, and 5-14 membered heteroaryl, or two R$^{bb}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

each instance of $R^{cc}$ is, independently, selected from hydrogen, $C_{1-10}$ alkyl, $C_{1-10}$ perhaloalkyl, $C_{2-10}$ alkenyl, $C_{2-10}$ alkynyl, heteroC$_{1-10}$ alkyl, heteroC$_{2-10}$ alkenyl, heteroC$_{2-10}$ alkynyl, $C_{3-10}$ carbocyclyl, 3-14 membered heterocyclyl, $C_{6-14}$ aryl, and 5-14 membered heteroaryl, or two $R^{cc}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups;

each instance of $R^{dd}$ is, independently, selected from halogen, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(R$^{ff}$)$_3^+$X$^-$, —N(OR$^{ee}$)R$^{ff}$, —SH, —SR$^{ee}$, —SSR$^{ee}$, —C(=O)R$^{ee}$, —CO$_2$H, —CO$_2$R$^{ee}$, —OC(=O)R$^{ee}$, —OCO$_2$R$^{ee}$, —C(=O)N(R$^{ff}$)$_2$, —OC(=O)N(R$^{ff}$)$_2$, —NR$^{ff}$C(=O)R$^{ee}$, —NR$^{ff}$CO$_2$R$^{ee}$, —NR$^{ff}$C(=O)N(R$^{ff}$)$_2$, —C(=NR$^{ff}$)OR$^{ee}$, —OC(=NR$^{ff}$)R$^{ee}$, —OC(=NR$^{ff}$)OR$^{ee}$, —C(=NR$^{ff}$)N(R$^{ff}$)$_2$, —OC(=NR$^{ff}$)N(R$^{ff}$)$_2$, —NR$^{ff}$C(=NR$^{ff}$)N(R$^{ff}$)$_2$, —NR$^{ff}$SO$_2$R$^{ee}$, —SO$_2$N(R$^{ff}$)$_2$, —SO$_2$R$^{ee}$, —SO$_2$OR$^{ee}$, —OSO$_2$R$^{ee}$, —S(=O)R$^{ee}$, —Si(R$^{ee}$)$_3$, —OSi(R$^{ee}$)$_3$, —C(=S)N(R$^{ff}$)$_2$, —C(=O)SR$^{ee}$, —C(=S)SR$^{ee}$, —SC(=S)SR$^{ee}$, —P(=O)$_2$R$^{ee}$, —P(=O)(R$^{ee}$)$_2$, —OP(=O)(R$^{ee}$)$_2$, —OP(=O)(OR$^{ee}$)$_2$, $C_{1-6}$ alkyl, $C_{1-6}$ perhaloalkyl, $C_{2-6}$ alkenyl, $C_{2-6}$ alkynyl, heteroC$_{1-6}$ alkyl, heteroC$_{2-6}$ alkenyl, heteroC$_{2-6}$alkynyl, $C_{3-10}$ carbocyclyl, 3-10 membered heterocyclyl, $C_{6-10}$ aryl, 5-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{gg}$ groups, or two geminal $R^{dd}$ substituents can be joined to form =O or =S;

each instance of $R^{ee}$ is, independently, selected from $C_{1-6}$ alkyl, $C_{1-6}$ perhaloalkyl, $C_{2-6}$ alkenyl, $C_{2-6}$ alkynyl, heteroC$_{1-6}$ alkyl, heteroC$_{2-6}$ alkenyl, heteroC$_{2-6}$alkynyl, $C_{3-10}$ carbocyclyl, $C_{6-10}$ aryl, 3-10 membered heterocyclyl, and 3-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{gg}$ groups;

each instance of $R^{ff}$ is, independently, selected from hydrogen, $C_{1-6}$ alkyl, $C_{1-6}$ perhaloalkyl, $C_{2-6}$ alkenyl, $C_{2-6}$ alkynyl, heteroC$_{1-6}$ alkyl, heteroC$_{2-6}$ alkenyl, heteroC$_{2-6}$ alkynyl, $C_{3-10}$ carbocyclyl, 3-10 membered heterocyclyl, $C_{6-10}$ aryl and 5-10 membered heteroaryl, or two $R^{ff}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{gg}$ groups; and each instance of $R^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3^+$X$^-$, —NH(C$_{1-6}$ alkyl)$_2^+$X$^-$, —NH$_2$(C$_{1-6}$ alkyl)$^+$X$^-$, —NH$_3^+$X$^-$, —N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl), —C(=O)(C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$ alkyl)$_2$, —OC(=O)NH(C$_{1-6}$ alkyl), —NHC(=O)(C$_{1-6}$ alkyl), —N(C$_{1-6}$ alkyl)C(=O)(C$_{1-6}$ alkyl), —NHCO$_2$(C$_{1-6}$ alkyl), —NHC(=O)N(C$_{1-6}$ alkyl)$_2$, —NHC(=O)NH(C$_{1-6}$ alkyl), —NHC(=O)NH$_2$, —C(=NH)O(C$_{1-6}$ alkyl), —OC(=NH)(C$_{1-6}$ alkyl), —OC(=NH)OC$_{1-6}$ alkyl, —C(=NH)N(C$_{1-6}$ alkyl)$_2$, —C(=NH)NH(C$_{1-6}$ alkyl), —C(=NH)NH$_2$, —OC(=NH)N(C$_{1-6}$ alkyl)$_2$, —OC(NH)NH(C$_{1-6}$ alkyl), —OC(NH)NH$_2$, —NHC(NH)N(C$_{1-6}$ alkyl)$_2$, —NHC(=NH)NH$_2$, —NHSO$_2$(C$_{1-6}$ alkyl), —SO$_2$N(C$_{1-6}$ alkyl)$_2$, —SO$_2$NH(C$_{1-6}$ alkyl), —SO$_2$NH$_2$, —SO$_2$C$_{1-6}$ alkyl, —SO$_2$OC$_{1-6}$ alkyl, —OSO$_2$C$_{1-6}$ alkyl, —SOC$_{1-6}$ alkyl, —Si(C$_{1-6}$ alkyl)$_3$, —OSi(C$_{1-6}$ alkyl)$_3$-C(=S)N(C$_{1-6}$ alkyl)$_2$, C(=S)NH(C$_{1-6}$ alkyl), C(=S)NH$_2$, —C(=O)S(C$_{1-6}$ alkyl), —C(=S)SC$_{1-6}$ alkyl, —SC(=S)SC$_{1-6}$ alkyl, —P(=O)$_2$(C$_{1-6}$ alkyl), —P(=O)(C$_{1-6}$ alkyl)$_2$, —OP(=O)(C$_{1-6}$ alkyl)$_2$, —OP(=O)(OC$_{1-6}$ alkyl)$_2$, $C_{1-6}$ alkyl, $C_{1-6}$ perhaloalkyl, $C_{2-6}$ alkenyl, $C_{2-6}$ alkynyl, heteroC$_{1-6}$ alkyl, heteroC$_{2-6}$ alkenyl, heteroC$_{2-6}$ alkynyl, $C_{3-10}$ carbocyclyl, $C_{6-10}$ aryl, 3-10 membered heterocyclyl, 5-10 membered heteroaryl; or two geminal $R^{gg}$ substituents can be joined to form =O or =S; wherein X$^-$ is a counterion.

As used herein, the term "halo" or "halogen" refers to fluorine (fluoro, —F), chlorine (chloro, —Cl), bromine (bromo, —Br), or iodine (iodo, —I).

As used herein, a "counterion" is a negatively charged group associated with a positively charged quarternary amine in order to maintain electronic neutrality. Exemplary counterions include halide ions (e.g., F$^-$, Cl$^-$, Br$^-$, I$^-$), NO$_3^-$, ClO$_4^-$, OH$^-$, H$_2$PO$_4^-$, HSO$_4^-$, sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), and carboxylate ions (e.g., acetate, ethanoate, propanoate, benzoate, glycerate, lactate, tartrate, glycolate, and the like).

As used herein, the term "hydroxyl" or "hydroxy" refers to the group —OH. The term "substituted hydroxyl" or "substituted hydroxyl," by extension, refers to a hydroxyl group wherein the oxygen atom directly attached to the parent molecule is substituted with a group other than hydrogen, and includes groups selected from —OR$^{aa}$, —ON(R$^{bb}$)$_2$, —OC(=O)SR$^{aa}$, —OC(=O)R$^{aa}$, —OCO$_2$R$^{aa}$, —OC(=O)N(R$^{bb}$)$_2$, —OC(=NR$^{bb}$)R$^{aa}$, —OC(=NR$^{bb}$)OR$^{aa}$, —OC(=NR$^{bb}$)N(R$^{bb}$)$_2$, —OS(=O)R$^{aa}$, —OSO$_2$R$^{aa}$, —OSi(R$^{aa}$)$_3$, —OP(R$^{cc}$)$_2$, —OP(R$^{cc}$)$_3$, —OP(=O)$_2$R$^{aa}$, —OP(=O)(R$^{aa}$)$_2$, —OP(=O)(OR$^{cc}$)$_2$, —OP(=O)$_2$N(R$^{bb}$)$_2$, and —OP(=O)(NR$^{bb}$)$_2$, wherein R$^{aa}$, R$^{bb}$, and R$^{cc}$ are as defined herein.

As used herein, the term "thiol" or "thio" refers to the group —SH. The term "substituted thiol" or "substituted thio," by extension, refers to a thiol group wherein the sulfur atom directly attached to the parent molecule is substituted with a group other than hydrogen, and includes groups selected from —SR$^{aa}$, —S=SR$^{cc}$, —SC(=S)SR$^{aa}$, —SC(=O)SR$^{aa}$, —SC(=O)OR$^{aa}$, and —SC(=O)R$^{aa}$, wherein R$^{aa}$ and R$^{cc}$ are as defined herein.

As used herein, the term, "amino" refers to the group —NH$_2$. The term "substituted amino," by extension, refers to a monosubstituted amino, a disubstituted amino, or a trisubstituted amino, as defined herein. In certain embodiments, the "substituted amino" is a monosubstituted amino or a disubstituted amino group.

As used herein, the term "monosubstituted amino" refers to an amino group wherein the nitrogen atom directly attached to the parent molecule is substituted with one hydrogen and one group other than hydrogen, and includes groups selected from —NH(R$^{bb}$), —NHC(=O)R$^{aa}$, —NHCO$_2$R$^{aa}$, —NHC(=O)N(R$^{bb}$)$_2$, —NHC(=NR$^{bb}$)N(R$^{bb}$)$_2$, —NHSO$_2$R$^{aa}$, —NHP(=O)(OR$^{cc}$)$_2$, and —NHP(=O)(NR$^{bb}$)$_2$, wherein R$^{aa}$, R$^{bb}$ and R$^{cc}$ are as defined herein, and wherein R$^{bb}$ of the group —NH(R$^{bb}$) is not hydrogen.

As used herein, the term "disubstituted amino" refers to an amino group wherein the nitrogen atom directly attached to the parent molecule is substituted with two groups other than hydrogen, and includes groups selected from —N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —NR$^{bb}$C(=NR$^{bb}$)N(R$^{bb}$)$_2$, —NR$^{bb}$SO$_2$R$^{aa}$, —NR$^{bb}$P(=O)(OR$^{cc}$)$_2$, and —NR$^{bb}$P(=O)(NR$^{bb}$)$_2$, wherein R$^{aa}$, R$^{bb}$, and R$^{cc}$ are as defined herein, with the proviso that the nitrogen atom directly attached to the parent molecule is not substituted with hydrogen.

As used herein, the term "trisubstituted amino" refers to an amino group wherein the nitrogen atom directly attached to the parent molecule is substituted with three groups, and includes groups selected from —N(R$^{bb}$)$_3$ and —N(R$^{bb}$)$_3$$^+$X$^-$, wherein R$^{bb}$ and X$^-$ are as defined herein.

Nitrogen atoms can be substituted or unsubstituted as valency permits, and include primary, secondary, tertiary, and quarternary nitrogen atoms. Exemplary nitrogen atom substitutents include, but are not limited to, hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{bb}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2$R$^{aa}$, —P(=O)(R$^{aa}$)$_2$, —P(=O)$_2$N(R$^{cc}$)$_2$, —P(=O)(NR$^{cc}$)$_2$, C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl, or two R$^{cc}$ groups attached to an N atom are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups, and wherein R$^{aa}$, R$^{bb}$, R$^{cc}$ and R$^{dd}$ are as defined above.

In certain embodiments, the substituent present on the nitrogen atom is an nitrogen protecting group (also referred to herein as an "amino protecting group"). Nitrogen protecting groups include, but are not limited to, —OH, —OR$^{aa}$, —N(R$^{cc}$)$_2$, —C(=O)R$^{aa}$, —C(=O)N(R$^{cc}$)$_2$, —CO$_2$R$^{aa}$, —SO$_2$R$^{aa}$, —C(=NR$^{cc}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, C$_{1-10}$ alkyl (e.g., aralkyl, heteroaralkyl), C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl groups, wherein each alkyl, alkenyl, alkynyl, heteroalkyl, heteroalkenyl, heteroalkynyl, carbocyclyl, heterocyclyl, aralkyl, aryl, and heteroaryl is independently substituted with 0, 1, 2, 3, 4, or 5 R$^{dd}$ groups, and wherein R$^{aa}$, R$^{bb}$, R$^{cc}$ and R$^{dd}$ are as defined herein. Nitrogen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

For example, nitrogen protecting groups such as amide groups (e.g., —C(=O)R$^{aa}$) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitophenylacetamide, o-nitrophenoxyacetamide, acetoacetamide, (N'-dithiobenzyloxyacylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide and o-(benzoyloxymethyl)benzamide.

Nitrogen protecting groups such as carbamate groups (e.g., —C(=O)OR$^{aa}$) include, but are not limited to, methyl carbamate, ethyl carbamante, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isobornyl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium)benzyl carbamate, and 2,4,6-trimethylbenzyl carbamate.

Nitrogen protecting groups such as sulfonamide groups (e.g., —S(=O)$_2$R$^{aa}$) include, but are not limited to, p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other nitrogen protecting groups include, but are not limited to, phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene)amine, N,N'-isopropylidenediamine, N-p-nitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexenyl) amine, N-borane derivative, N-diphenylborinic acid derivative, N-[phenyl(pentaacylchromium- or tungsten)acyl] amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys).

In certain embodiments, the substituent present on an oxygen atom is an oxygen protecting group (also referred to herein as an "hydroxyl protecting group"). Oxygen protecting groups include, but are not limited to, —$R^{aa}$, —$N(R^{bb})_2$, —$C(=O)SR^{aa}$, —$C(=O)R^{aa}$, —$CO_2R^{aa}$, —$C(=O)N(R^{bb})_2$, —$C(=NR^{bb})R^{aa}$, —$C(=NR^{bb})OR^{aa}$, —$C(=NR^{bb})N(R^{bb})_2$, —$S(=O)R^{aa}$, —$SO_2R^{aa}$, —$Si(R^{aa})_3$, —$P(R^{cc})_2$, —$P(R^{cc})_3$, —$P(=O)_2R^{aa}$, —$P(=O)(R^{aa})_2$, —$P(=O)(OR^{cc})_2$, —$P(=O)_2N(R^{bb})_2$, and —$P(=O)(NR^{bb})_2$, wherein $R^{aa}$, $R^{bb}$, and $R^{cc}$ are as defined herein. Oxygen protecting groups are well known in the art and include those described in detail in *Protecting Groups in Organic Synthesis*, T. W. Greene and P. G. M. Wuts, $3^{rd}$ edition, John Wiley & Sons, 1999, incorporated herein by reference.

Exemplary oxygen protecting groups include, but are not limited to, methyl, methoxylmethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy) ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 3-(imidazol-1-yl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), alkyl methyl carbonate, 9-fluorenylmethyl carbonate (Fmoc), alkyl ethyl carbonate, alkyl 2,2,2-trichloroethyl carbonate (Troc), 2-(trimethylsilyl)ethyl carbonate (TMSEC), 2-(phenylsulfonyl)ethyl carbonate (Psec), 2-(triphenylphosphonio) ethyl carbonate (Peoc), alkyl isobutyl carbonate, alkyl vinyl carbonate alkyl allyl carbonate, alkyl p-nitrophenyl carbonate, alkyl benzyl carbonate, alkyl p-methoxybenzyl carbonate, alkyl 3,4-dimethoxybenzyl carbonate, alkyl o-nitrobenzyl carbonate, alkyl p-nitrobenzyl carbonate, alkyl S-benzyl thiocarbonate, 4-ethoxy-1-napththyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxyacyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts).

In certain embodiments, the substituent present on an sulfur atom is a sulfur protecting group (also referred to as a "thiol protecting group"). Sulfur protecting groups include, but are not limited to, —$R^{aa}$, —$N(R^{bb})_2$, —$C(=O)SR^{aa}$, —$C(=O)R^{aa}$, —$CO_2R^{aa}$, —$C(=O)N(R^{bb})_2$, —$C(=NR^{bb})R^{aa}$, —$C(=NR^{bb})OR^{aa}$, —$C(=NR^{bb})N(R^{bb})_2$, —$S(=O)R^{aa}$, —$SO_2R^{aa}$, $Si(R^{aa})_3$, —$P(R^{cc})_2$, —$P(R^{cc})_3$, —$P(=O)_2R^{aa}$, —$P(=O)(R^{aa})_2$, —$P(=O)(OR^{cc})_2$, —$P(=O)_2N(R^{bb})_2$, and —P(═O)(NR$^{bb}$)$_2$, wherein R$^{aa}$, R$^{bb}$, and R$^{cc}$ are as defined herein. Sulfur protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

These and other exemplary substituents are described in more detail in the Detailed Description, Examples, and claims. The invention is not intended to be limited in any manner by the above exemplary listing of substituents.

OTHER DEFINITIONS

The term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, Berge et al., describes pharmaceutically acceptable salts in detail in *J. Pharmaceutical Sciences* (1977) 66:1-19. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Pharmaceutically acceptable salts derived from appropriate bases include alkali metal, alkaline earth metal, ammonium and N$^+$(C$_{1-4}$alkyl)$_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

"Disease", "disorder," and "condition" are used interchangeably herein.

As used herein, an "individual" or "subject" to which administration is contemplated includes, but is not limited to, humans (i.e., a male or female of any age group, e.g., a pediatric subject (e.g., child, adolescent) or adult subject (e.g., young adult, middle-aged adult or senior adult)), other primates (e.g., cynomolgus monkeys, rhesus monkeys) and commercially relevant mammals such as cattle, pigs (e.g., livestock, minipigs), horses, sheep, goats, cats, and/or dogs. In any aspect and/or embodiment of the invention, the mammal can be a human.

As used herein, "local administration" or "administering locally" or "local effect" means administration/application of the active ingredient or active metabolite thereof directly, or in proximity to, a part of the body, tissue, or lesion where said active substance is intended to exert its action. This may include, for example, topical administration to skin or injection at the part of the body where an increase of fat is needed.

As used herein, "percutaneous" or "percutaneous administration" or "percutaneous delivery" or "percutaneously administering" or "percutaneously delivering" means administration to or through the skin that results in a local effect on subcutaneous fat without a corresponding, clinically significant systemic effect. With superficial skin delivery, the drug remains on or within the skin. With transdermal delivery, system exposure to the drug is sufficient to result in a clinically significant systemic effect. In contrast, with percutaneous delivery, the drug passes into the subcutaneous fat, but systemic exposure is negligible, e.g., it does not cause a clinically significant systemic effect. See, e.g., FIG. 1.

As used herein, "systemic" refers to an action or effect that occurs in one or more part(s) of the body other than that part of the body where a drug is administered or intended to exert its action.

A "corresponding systemic effect" is manifested, for example, when the drug's local effect at the site of administration is also seen at a site on the body that is distant from the site of administration. For example, administration of a drug to one side (e.g., flank) of the body resulting in a increased fat on both sides of the body would indicate a systemic effect. Conversely, with percutaneous administration, subcutaneous fat at the treatment site is increased with respect to subcutaneous fat on a control site.

As used herein, a "clinically significant systemic effect" means a systemic effect that is large enough to affect a patient's health, disease state, or risk of disease in a manner that is noticeable to the patient and/or caregiver. See, e.g., Jonas et al. Drug Class Review: Newer diabetes medications, TZDs, and combinations. Final Original Report. *Drug Effectiveness Review Project*, February 2011. The effect can be immediate or delayed; for example, a patient with abnormally elevated serum glucose concentrations (diabetes) may not immediately notice the diabetes, but the diabetes eventually noticeably affects the patient's health, for example, by renal impairment, heart disease, and vision loss. As a further example, assume that a patient with diabetes has a hemoglobin A1C value (a long-term marker of glucose control) that is elevated at 8.00%. An effect that changes the hemoglobin A1C value to 7.99 or 8.01 would not be clinically significant, because it would not affect the occurrence or risk of renal impairment, heart disease, or vision loss. However, an effect that changes the hemoglobin A1C value to 7.00 or 9.00 would be clinically significant, insofar as it would affect the occurrence or risk of the aforementioned outcomes.

As used herein, a "percutaneous carrier" or "percutaneous excipient" means a carrier that, when combined with one or more active ingredients and administered to the subject, results in a local effect on subcutaneous fat without a clinically significant systemic effect.

As used herein, a "treatment site" is the place on the body where the drug is administered.

As used herein, a "control site" is a place on a body suitable for use as a control in a controlled experiment. The control site can be a place on the body that is comparable to the treatment site (e.g., contralateral) but is untreated or treated with a placebo (e.g., inactive vehicle). The control site and the treatment site can be on the same subject or on different subjects.

As used herein, unless otherwise defined by the context, "anhydrous" refers to a composition that is lacking or essentially lacking in water, e.g., for example, if no water is added to the composition, and/or if water is removed from the composition. For example, in certain embodiments, an anhydrous composition may consist of between about 0 and about 1 percent of water by weight, e.g., about 0%, about 0.1%, about 0.2%, about 0.3%, about 0.4%, about 0.5%, about 0.6%, about 0.7%, about 0.8%, about 0.9%, or about 1% of water by weight.

As used herein, and unless otherwise specified, a "therapeutically effective amount" "an amount sufficient" or "sufficient amount" of a compound means the level, amount or concentration of the compound needed to treat a disease, disorder or condition, or to improve a particular parameter (e.g., increase body fat, reduce wrinkles) in the body of a subject, without causing significant negative or adverse side effects to body or the treated tissue. The term "therapeutically effective amount" can encompass an amount that improves overall therapy, reduces or avoids symptoms or causes of disease or condition, or enhances the therapeutic efficacy of another therapeutically active agent.

As used herein, the terms "increase", "increasing", "raise", or "raising" means to increase or raise the volume, size, mass, bulk, density, amount, and/or quantity of a substance (e.g., body fat, adipose tissue) in the body of a subject.

As used herein, the terms "augment," "augmenting," and "augmentation" refer to increasing the size or prominence of a body part or particular area thereof. The size can be measured by any suitable measure (e.g., linear, circumferential, volumetric, mass). Suitable measures of size are envisioned to include, without limitation, histology (e.g., biopsy, necropsy) or non-invasive measures of subcutaneous fat depth (e.g., skin fold calipers, magnetic resonance imaging, computed tomography, dual-energy x-ray absorptiometry, ultrasound, and the like). Size is further envisioned, without limitation, to include external measurement of any human body part (e.g., a tailor's measurements, e.g., of the neck, chest, limbs, waist, hips) and sizing schemes used for articles of clothing and the like. Prominence can be anatomic or visual, absolute or measured with respect to another body part, and measured by any suitable objective or subjective variable, including a subjective rating scale.

As used herein, "suffer", "suffers" or "suffering from" refers to a subject diagnosed with a particular disease or condition. As used herein, "likely to suffer" refers to a subject who has not been diagnosed with a particular disease or condition by a medical practitioner, but has a predisposition (e.g., genetic and/or physiologic predisposition), or exhibits signs or symptoms of the disease or condition.

As used herein, and unless otherwise specified, the terms "treat," "treating" and "treatment" contemplate an action that occurs while a subject is suffering from the specified disease or condition, which reduces the severity of the disease or condition, or retards or slows the progression of the disease or condition.

As used herein, unless otherwise specified, the terms "prevent," "preventing" and "prevention" contemplate an action that occurs before a subject begins to suffer from the specified disease or condition, which inhibits or reduces the severity of the disease or condition.

As used herein, and unless otherwise specified, the term "medicament" means a substance administered to an individual to treat or prevent a disease or condition. Unless otherwise clear from the context, the terms "medicament," "medication," "medicine," and "pharmaceutical composition" are used interchangeably.

As used herein, the term "prodrug" means a compound that can hydrolyze, oxidize, or otherwise react under biological conditions (e.g., in vitro or in vivo enzymatic conditions) to provide a pharmacologically active compound. In certain cases, a prodrug has improved physical and/or delivery properties over the parent compound. Prodrugs are typically designed to enhance pharmacologically, pharmaceutically and/or pharmacokinetically based properties associated with the parent compound. The advantage of a prodrug can lie in its physical properties, such as enhanced solubility for formulation compared to the parent compound, or enhanced penetration across the stratum corneum of the skin, or enhanced deposition in the subcutaneous fat.

DETAILED DESCRIPTION OF CERTAIN EMBODIMENTS OF THE INVENTION

Figure 1:
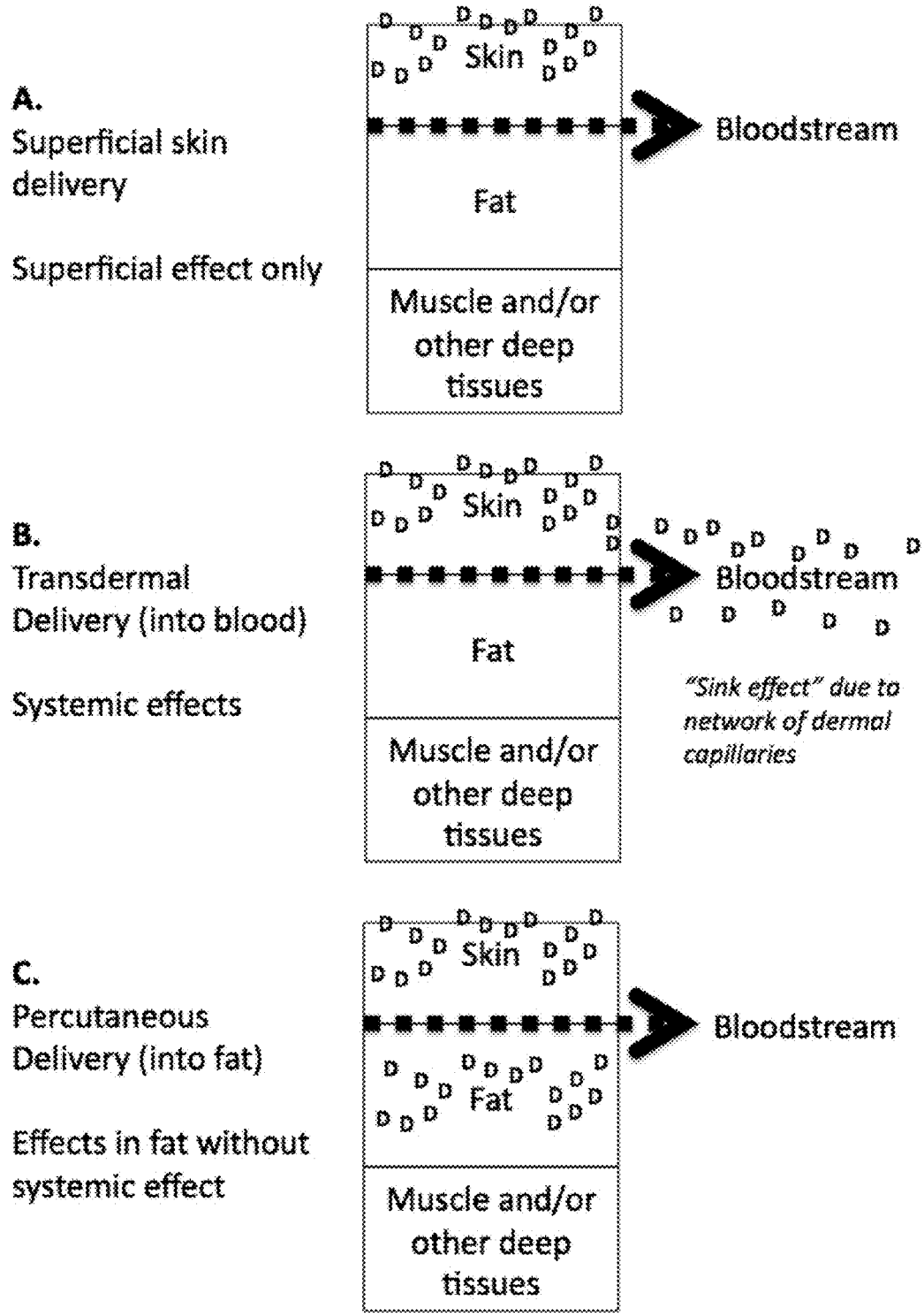
FIG. 1A-1C depicts a schematic diagram of superficial skin delivery (FIG. 1A), transdermal delivery into the bloodstream (FIG. 1B), and percutaneous delivery into fat (FIG. 1C). The relative presence or concentration of a drug is indicated by the letter "D." Note that with superficial skin delivery (FIG. 1A), the drug remains on or within the skin. With transdermal delivery (FIG. 1B), substantial amounts of the drug are absorbed in the dermal circulation and into the bloodstream, thus leading to systemic effects. With percutaneous delivery (FIG. 1C), drug passes into the subcutaneous fat, with negligible presence in the bloodstream.

The present invention arises from the realization that percutaneously administering a thiazolidinedione or an orexigenic compound to a subject effectively achieves a local increase in subcutaneous fat. This finding arose during an in vivo study in lean mice (Example 1), and was then corroborated and improved in further mouse and minipig studies (e.g., Examples 2 and 4) as well as in vitro studies of human skin (e.g., Example 5).

The first mouse study involved a control arm and four intervention arms, each with a different class of compound that when administered systemically to humans is known to promote obesity and fat accumulation.

The arms were as follows: vehicle (Lipoderm®), a thiazolidinedione (pioglitazone), harmine, an orexigenic compound (megestrol acetate), and efavirenz. Each compound was combined in the percutaneous Lipoderm® formulation at an equimolar concentration (5 mM). The Lipoderm® vehicle is adapted to deliver the respective compound percutaneously, i.e., across the skin and into subcutaneous fat. The formulations were applied daily to the right flank of each animal, whereas the left flank was used as an untreated control.

Following 24 days of therapy, animals treated with a thiazolidinedione (pioglitazone) or an orexigenic compound (megestrol acetate) exhibited local increases in subcutaneous fat (right flanks only). However, animals treated with vehicle, harmine, or efavirenz did not exhibit any increase in fat or asymmetry between the two flanks. The asymmetric increases in body fat seen in animals treated with pioglitazone and megestrol acetate were corroborated by modest increases in overall weight gain, as compared to animals in other groups.

The superiority of pioglitazone for increasing local fat in this study was unexpected, not least because harmine, another class of PPARγ activator with similar biophysical and pharmacokinetic properties, had no effect. Furthermore, although it had been hypothesized based solely on in vitro evidence that topical administration of a thiazolidinedione to an individual could locally increase body fat, no such effect has been observed in a clinical trial of a topically applied thiazolidinedione. See, e.g., Kuenzli and Saurat, *Dermatology* (2003) 206:252-256.

The superiority of megestrol acetate for increasing local fat in this study was also unexpected, because this compound's obesity-promoting action is believed to be due to appetite stimulation (which would have manifested as diffuse rather than local increases in fat in the aforementioned mouse study). Furthermore, subcutaneous implantation and/or transdermal administration of megestrol acetate has not been associated with fat accumulation at the site of administration, a side effect which almost certainly would have attracted the notice of clinical investigators, treating physicians, and patients. See, e.g., Coutinho, et al., *Contraception* (1996) 53:121-125.

The present invention also arises from the reduction to practice of a means for administering a thiazolidinedione or an orexigenic compound such that a therapeutic effect is achieved in local subcutaneous fat, without a systemic effect (which would have manifested as diffuse rather than local increases in fat in the aforementioned mouse study). This percutaneous mode of delivery is to be distinguished from superficial application to the skin, whereby deep penetration does not occur. See, e.g., FIG. 1. Percutaneous administration is also to be distinguished from transdermal administration, where the objective is absorption into the bloodstream to achieve a systemic effect. Transdermal administration of a thiazolidinedione, e.g., rosiglitazone, to the skin can result in clinically significant drug delivery to the bloodstream. See, e.g., Damodharan et al, Skin permeation of rosiglitazone from transdermal matrix patches, *Pharmaceutical Technology* (2010) 34:56-72. See also, e.g., Ghosh et al, Feasibility of rosiglitazone maleate for transdermal delivery, *Int. J. Pharm. Res. Innov.* (2011) 2:23-31. Transdermal administration of thiazolidinediones is considered undesirable and potentially unsafe and would undermine the purpose of the invention, e.g., by causing obesity. Transdermal administration of megestrol would be expected to cause obesity and act as a contraceptive, which for the present invention would be undesirable.

While superficial and transdermal administration are common pharmaceutical routes of administration, very few examples of percutaneous administration to subcutaneous fat are known for any compound. See, e.g., Singh et al., Local deep tissue penetration of compounds after dermal application: structure-tissue penetration relationships. *JPET* (1996) 279:908-917.

According to the present invention, thiazolidinediones and/or an orexigenic compounds, as described herein, are to be administered percutaneously (e.g., in a percutaneous formulation to the skin, or by injection through the skin) in order to achieve a local increase in subcutaneous body fat. The percutaneous administration confers two crucial advantages: the ability to limit therapy to a particular affected part of the body, and the ability to avoid systemic exposure (and therefore systemic risks and side effects).

Percutaneous administration can be directed to particular affected areas of the body of the subject, e.g., for example, the head (e.g., the face such as the forehead, forehead, periorbital region, cheeks, chin, lips, and other anterior structures from top of forehead to bottom of chin), breast, limbs, hands, trunk, hips, and buttocks. Without being bound by theory, increase in fat as a function of administration of a thiazolidinedione or an orexigenic compound as disclosed herein may include increasing the number of fat cells, increasing the volume of one or more fat cells, increasing maturation of one or more fat cells, and/or promoting differentiation of one or more fat cells.

Increasing fat can include increasing fat as measured by at least one of volume, size, mass, bulk, density, amount, and/or quantity. The present invention is expected to increase fat by greater than or equal to 75%, greater than or equal to 70%, greater than or equal to 60%, greater than or equal to 50%, greater than or equal to 40%, greater than or equal to 30%, greater than or equal to 25%, greater than or equal to 20%, greater than or equal to 15%, greater than or equal to 10%, or greater than or equal to 5%. For example, increasing fat can also include increasing fat cell amount (for example, fat cell number), increasing fat cell volume, increasing fat cell maturation, and/or promoting fat cell differentiation.

Thiazolidinedione Compounds

Thiazolidinediones are a class of medications previously approved for systemic administration for the treatment of type 2 diabetes mellitus. Thiazolidinediones specifically contemplated for use include, but are not limited to, rosiglitazone, pioglitazone, troglitazone, ciglitazone, netoglitazone, rivoglitazone, and pharmaceutically acceptable salts and prodrugs thereof.

Rosiglitazone, pioglitazone, and troglitazone were previously marketed for diabetes. However, these compounds have been withdrawn or restricted in most countries, and development of other thiazolidinediones has been abandoned, due to safety concerns, e.g., death, cardiovascular adverse events, bladder cancer, hepatitis, and bone fractures. Accordingly, health care practitioners and scientists have been strongly dissuaded from further use or development of thiazolidinediones. A known adverse effect of systemically administered thiazolidinediones is obesity and accumulation of body fat. See, e.g., Smith et al, *Metabolism* (2005) 54:24-32; Jacob et al, *Diabetes Obes Metab* (2007) 9:386-393; Kim et al, *Eur J Endocrinol* (2007) 157:167-174. This effect is widely attributed to the molecular action of these compounds, which is activation of Peroxisome Proliferator-Activated Receptor Gamma (PPARγ). The undesired tendency of systemic thiazolidinedione administration to promote obesity has nevertheless been exploited to increase body fat in individuals affected by lipodystrophy, e.g., HIV lipodystrophy. See, e.g., Slama et al, Antivir Ther (2008)13:67-76. Drawbacks of this systemic approach include the potential for serious side effects, e.g., cardiovascular adverse events, bladder cancer, and hepatitis, and the inability to direct therapy to a particular part of the body. Thus, systemic thiazolidinedione administration is viewed as impractical for the promotion of obesity, and a safer means is needed to achieve a local increase in body fat.

In contrast, the present invention contemplates percutaneous administration of thiazolidinediones for locally increasing body fat. For example, in one aspect, provided is a method for increasing fat locally in a subject in need thereof, the method comprising administering percutaneously to the subcutaneous fat of the subject a thiazolidinedione or pharmaceutically acceptable salt or prodrug thereof. In certain embodiments, the administering step comprises topical application to the skin using a percutaneous carrier, or by intradermal injection, subcutaneous injection, intramuscular injection, intralesional injection, transmucosal injection, or mucosal application.

In certain embodiments, the thiazolidinedione is a compound of Formula (I):

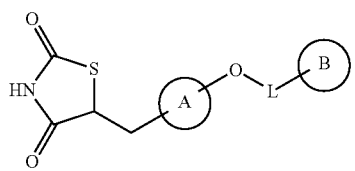

(I)

or a pharmaceutically acceptable salt or prodrug thereof; wherein:

Ring A is substituted or unsubstituted arylene or substituted or unsubstituted heteroarylene;

L is substituted or unsubstituted $C_{1-6}$alkylene or substituted or unsubstituted heteroC$_{1-6}$alkylene; and Ring B is substituted or unsubstituted carbocyclyl, substituted or unsubstituted heterocyclyl, substituted or unsubstituted aryl, or substituted or unsubstituted heteroaryl.

In certain embodiments, Ring A is substituted or unsubstituted arylene, e.g., substituted or unsubstituted phenylene or substituted or unsubstituted naphthylene. In certain embodiments, Ring A is substituted or unsubstituted phenylene.

In certain embodiments, Ring A is substituted or unsubstituted heteroarylene, e.g., a 6-membered heteroarylene such as substituted or unsubstituted pyridinylene.

In certain embodiments, L is substituted or unsubstituted $C_{1-6}$alkylene, e.g., substituted or unsubstituted $C_1$alkylene, substituted or unsubstituted $C_2$alkylene, substituted or unsubstituted $C_3$alkylene, substituted or unsubstituted $C_4$alkylene, substituted or unsubstituted $C_5$alkylene, or substituted or unsubstituted $C_6$alkylene. In certain embodiments, L is —CH$_2$—, —(CH$_2$)$_2$—, —(CH$_2$)$_3$—, —(CH$_2$)$_4$—, —(CH$_2$)$_5$—, or —(CH$_2$)$_6$—.

In certain embodiments, L is substituted or unsubstituted heteroC$_{1-6}$alkylene, e.g., substituted or unsubstituted heteroC$_1$alkylene, substituted or unsubstituted heteroC$_2$alkylene, substituted or unsubstituted heteroC$_3$alkylene, substituted or unsubstituted heteroC$_4$alkylene, substituted or unsubstituted heteroC$_5$alkylene, or substituted or unsubstituted heteroC$_6$alkylene. In certain embodiments, L is —CH$_2$(Y)—, —(CH$_2$)$_2$(Y)—, —(CH$_2$)$_3$(Y)—, —(CH$_2$)$_4$(Y)—, —(CH$_2$)$_5$(Y)—, or —(CH$_2$)$_6$(Y)—, wherein Y is O, S, or NR$^L$, and R$^L$ is hydrogen, a nitrogen protecting group, or $C_{1-6}$alkyl (e.g., methyl). In certain embodiments, Y is NR$^L$, and R$^L$ is hydrogen or methyl.

In certain embodiments, Ring B is substituted or unsubstituted carbocyclyl, e.g., substituted or unsubstituted $C_{5-6}$ carbocyclyl. In certain embodiments, Ring B is substituted or unsubstituted cyclopentyl. In certain embodiments, Ring B is substituted or unsubstituted cyclohexyl.

In certain embodiments, Ring B is substituted or unsubstituted heterocyclyl, e.g., a 5- to 6-membered heterocyclyl. In certain embodiments, the heterocyclyl ring comprises a substituted or unsubstituted aryl or substituted or unsubstituted heteroaryl ring fused thereto, wherein the point of attachment is on the heterocyclyl ring. In certain embodiments, Ring B is a 6-membered substituted or unsubstituted heterocyclyl, e.g., a substituted or unsubstituted dihydropyranyl comprising a substituted or unsubstituted aryl ring fused thereto, also referred to as substituted or unsubstituted chromanyl.

In certain embodiments, Ring B is substituted or unsubstituted aryl, e.g., substituted or unsubstituted phenyl or substituted or unsubstituted naphthyl. In certain embodiments, Ring B is substituted or unsubstituted phenyl.

In certain embodiments, Ring B is substituted or unsubstituted heteroaryl. In certain embodiments, Ring B is a substituted or unsubstituted 6-membered heteroaryl, e.g., substituted or unsubstituted pyridinyl. In certain embodiments, Ring B is a substituted or unsubstituted bicyclic heteroaryl, e.g., a substituted or unsubstituted 5,6-bicyclic heteroaryl, e.g., substituted or unsubstituted benzimidazolyl.

Various combinations of the above embodiments are contemplated herein.

For example, in certain embodiments, wherein Ring A is phenylene, provided is a compound of Formula (I-a):

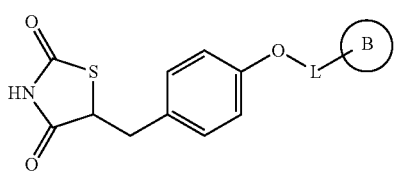

(I-a)

or a pharmaceutically acceptable salt or prodrug thereof. In certain embodiments, L is —CH$_2$(Y)— or —(CH$_2$)$_2$(Y)—, wherein Y is O, S, or NR$^L$. In certain embodiments, L is —CH$_2$—, —(CH$_2$)$_2$—, or —(CH$_2$)$_3$—. In certain embodiments, Ring B is substituted or unsubstituted cyclohexyl. In certain embodiments, Ring B is a substituted or unsubstituted chromanyl. In certain embodiments, Ring B is substituted or unsubstituted phenyl. In certain embodiments, Ring B is substituted or unsubstituted heteroaryl, e.g., substituted or unsubstituted pyridinyl or substituted or unsubstituted benzimidazolyl.

In certain embodiments, wherein Ring A is naphthylene, provided is a compound of Formula (I-b):

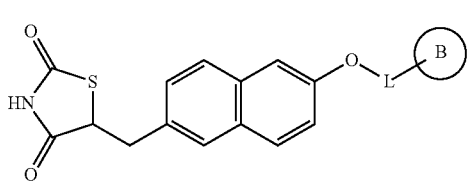

(I-b)

or a pharmaceutically acceptable salt or prodrug thereof. In certain embodiments, L is —CH$_2$(Y)— or —(CH$_2$)$_2$(Y)—, wherein Y is O, S, or NR$^L$. In certain embodiments, L is —CH$_2$—, —(CH$_2$)$_2$—, or —(CH$_2$)$_3$—. In certain embodiments, Ring B is substituted or unsubstituted cyclohexyl. In certain embodiments, Ring B is a substituted or unsubstituted chromanyl. In certain embodiments, Ring B is substituted or unsubstituted phenyl. In certain embodiments, Ring B is substituted or unsubstituted heteroaryl, e.g., substituted or unsubstituted pyridinyl or substituted or unsubstituted benzimidazolyl.

Exemplary compounds of Formula (I) include, but are not limited to:

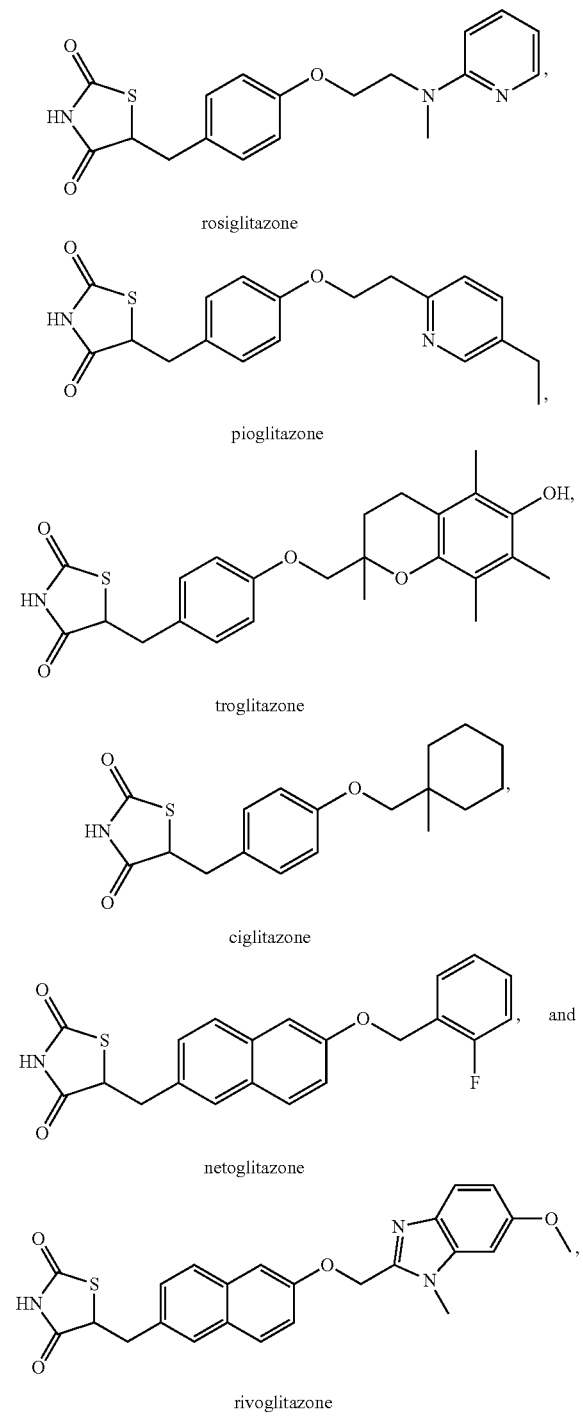

rosiglitazone pioglitazone troglitazone ciglitazone netoglitazone rivoglitazone and pharmaceutically acceptable salts thereof and prodrugs thereof.

Orexigenic Compounds

Pregnane derivatives are a class of steroid derivatives with carbons present at positions 1 through 21. As used herein, an "orexigenic compound" means a pregnane or pregnene (e.g., pregnene, pregnadiene, or pregnatriene) compound that, when administered systemically to a subject, stimulates the appetite and/or food intake. Orexigenic compounds specifically contemplated for use in the invention include, but are not limited to, megestrol, megestrol acetate, medroxyprogesterone, medroxyprogesterone acetate, and pharmaceutically acceptable salts and prodrugs thereof.

When administered systemically, megestrol acetate stimulates appetite by central mechanisms, and is therefore used to increase caloric balance and promote weight gain, e.g., in patients with cancer- or HIV-associated cachexia. Megestrol acetate is also used as a contraceptive and as an antineoplastic agent, e.g., in the treatment of breast, endometrial, and prostate cancers. Although systemic administration of megestrol acetate causes weight gain and/or obesity, it does not increase breast tissue. On the contrary, the endocrine profile of megestrol acetate is such that it inhibits breast tissue.

In contrast, the present invention contemplates percutaneous administration of an orexigenic compound for locally increasing body fat. For example, in another aspect, provided is a method for increasing fat locally in a subject in need thereof, the method comprising administering percutaneously to the subcutaneous fat of the subject an orexigenic compound, or a pharmaceutically acceptable salt or prodrug thereof. In certain embodiments, the administering step comprises topical application to the skin using a percutaneous carrier, or by intradermal injection, subcutaneous injection, intramuscular injection, intralesional injection, transmucosal injection, or mucosal application.

In some embodiments, an orexigenic compound is a compound that, when administered systemically to a subject, causes a mean daily caloric intake in the subject that is greater than or equal to 200% of control, greater than or equal to 150% of control, greater than or equal to 125% of control, greater than or equal to 110% of control, greater than or equal to 105% of control, or greater than or equal to 100% of control, e.g., between about 100% to about 500%, between about 100% to about 200%, between about 300% to about 400%, or between about 400% to about 500% of control.

In certain embodiments, the orexigenic compound is a compound of Formula (II):

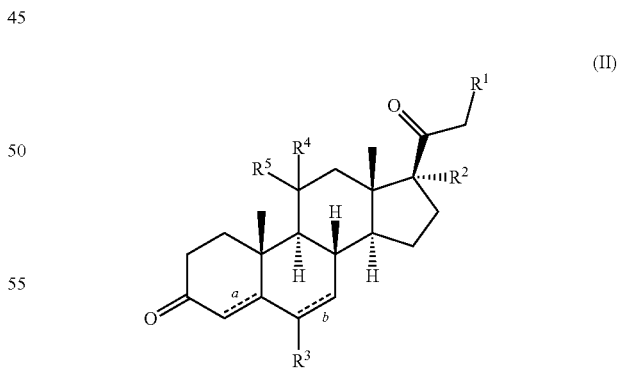

(II)

or a pharmaceutically acceptable salt or prodrug thereof;
wherein:
each instance of ----- independently represents a single or double bond;
R$^1$ is hydrogen, hydroxyl, substituted hydroxyl, thiol, substituted thiol, amino, or substituted amino;
R$^2$ is hydrogen, hydroxyl, substituted hydroxyl, thiol, substituted thiol, amino, or substituted amino;

$R^3$ is hydrogen or substituted or unsubstituted $C_{1-6}$alkyl;

$R^4$ is hydrogen, hydroxyl, substituted hydroxyl, thiol, substituted thiol, amino, or substituted amino, and $R^5$ is hydrogen; or $R^4$ and $R^5$ are joined to form an oxo group =O.

In certain embodiments, ----- designated as "b" represents a double bond. In certain embodiments, ----- designated as "a" represents a double bond. In certain embodiments, each instance of ----- represents a double bond.

However, in certain embodiments, ----- designated as "b" represents a single bond. In certain embodiments, ----- designated as "a" represents a single bond, and in such an instance, the hydrogen at C5 is provided in the alpha or beta configuration. In certain embodiments, each instance of ----- represents a single bond.

In certain embodiments, ----- designated as "b" represents a single bond, and ----- designated as "a" represents a double bond. In certain embodiments, ----- designated as "a" represents a single bond, and ----- designated as "b" represents a double bond.

In certain embodiments, $R^1$ is hydrogen. In certain embodiments, $R^1$ is hydroxyl. In certain embodiments, $R^1$ is substituted hydroxyl. In certain embodiments, $R^1$ is thiol. In certain embodiments, $R^1$ is substituted thiol. In certain embodiments, $R^1$ is amino. In certain embodiments, $R^1$ is substituted amino.

In certain embodiments, $R^2$ is hydrogen. In certain embodiments, $R^2$ is hydroxyl. In certain embodiments, $R^2$ is substituted hydroxyl. In certain embodiments, $R^2$ is thiol. In certain embodiments, $R^2$ is substituted thiol. In certain embodiments, $R^2$ is amino. In certain embodiments, $R^2$ is substituted amino.

In certain embodiments, $R^3$ is hydrogen. In certain embodiments, $R^3$ is substituted or unsubstituted $C_{1-6}$alkyl, e.g., substituted or unsubstituted $C_1$alkyl, substituted or unsubstituted $C_2$alkyl, substituted or unsubstituted $C_3$alkyl, substituted or unsubstituted $C_4$alkyl, substituted or unsubstituted $C_5$alkyl, or substituted or unsubstituted $C_6$alkyl. In certain embodiments, $R^3$ is —$CH_3$ or —$CH_2CH_3$.

In certain embodiments, $R^4$ is hydrogen and $R^5$ is hydrogen. In certain embodiments, $R^4$ is hydroxyl and $R^5$ is hydrogen. In certain embodiments, $R^4$ is substituted hydroxyl and $R^5$ is hydrogen. In certain embodiments, $R^4$ is thiol and $R^5$ is hydrogen. In certain embodiments, $R^4$ is substituted thiol and $R^5$ is hydrogen. In certain embodiments, $R^4$ is amino and $R^5$ is hydrogen. In certain embodiments, $R^4$ is substituted amino and $R^5$ is hydrogen. In certain embodiments, $R^4$ and $R^5$ are joined to form an oxo group =O.

Various combinations of the above embodiments are contemplated herein.

For example, in certain embodiments, each instance of ----- represents a double bond, provided is a compound of Formula (II-a):

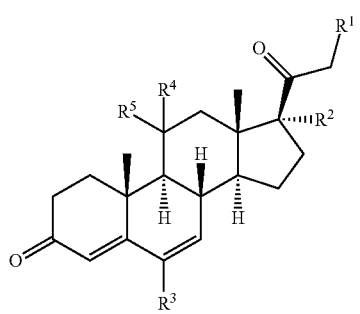

(II-a)

or a pharmaceutically acceptable salt or prodrug thereof. In certain embodiments, $R^1$ is hydrogen. In certain embodiments, $R^2$ is hydroxyl. In certain embodiments, $R^2$ is substituted hydroxyl, e.g., —OC(=O)$R^{aa}$, wherein $R^{aa}$ is substituted or unsubstituted $C_{1-10}$alkyl. In certain embodiments, $R^4$ is hydrogen and $R^5$ is hydrogen. In certain embodiments, $R^3$ is substituted or unsubstituted $C_{1-6}$alkyl, e.g., $R^3$ is —$CH_3$.

In certain embodiments, wherein ----- designated as "b" represents a single bond, and ----- designated as "a" represents a double bond, provided is a compound of Formula (II-b):

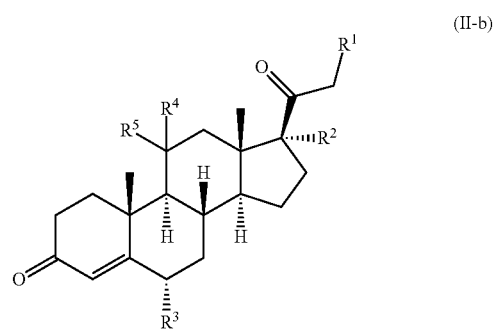

(II-b)

or a pharmaceutically acceptable salt or prodrug thereof. In certain embodiments, $R^1$ is hydrogen. In certain embodiments, $R^2$ is hydroxyl. In certain embodiments, $R^2$ is substituted hydroxyl, e.g., —OC(=O)$R^{aa}$, wherein $R^{aa}$ is substituted or unsubstituted $C_{1-10}$alkyl. In certain embodiments, $R^4$ is hydrogen and $R^5$ is hydrogen. In certain embodiments, $R^3$ is substituted or unsubstituted $C_{1-6}$alkyl, e.g., $R^3$ is —$CH_3$. In certain embodiments, ----- designated as "b" represents a single bond, and ----- designated as "a" represents a double bond. In certain embodiments, each instance of ----- represents a double bond.

Exemplary compounds of Formula (II) include, but are not limited to:

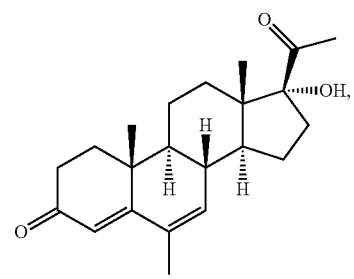

megestrol

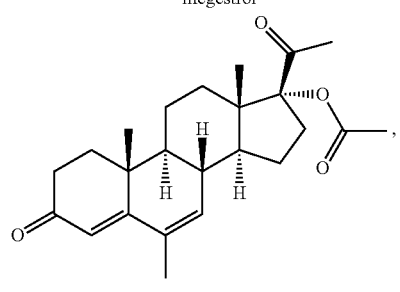

megestrol acetate

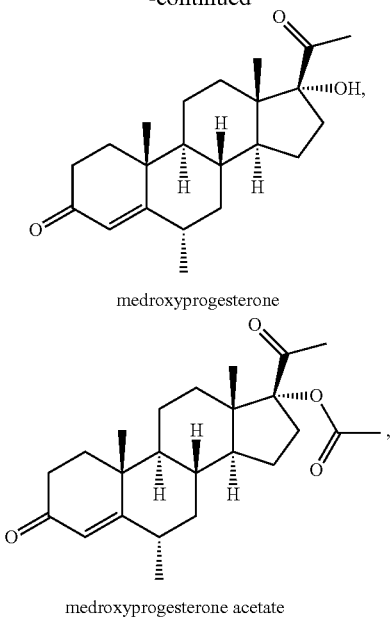

medroxyprogesterone medroxyprogesterone acetate and pharmaceutically acceptable salts and prodrugs thereof.

Use of Prodrugs According to the Invention

Without being bound by any particular theory, it is understood that one or more of the above described compounds contemplated for administration to a subject can exist as prodrugs. Accordingly, and without being bound by theory, the invention envisions, for example, that analogs of the above compounds may comprise esters (e.g., —OC(=O)R$^{aa}$ or —C(=O)OR$^{aa}$ wherein R$^{aa}$ is defined herein) and/or amides (e.g., —NR$^{bb}$C(=O)R$^{aa}$ or —C(=O)N(R$^{bb}$)$_2$ wherein R$^{aa}$ and R$^{bb}$ are as defined herein) that are substrates for hydrolases in the skin (e.g., esterases, amidases). It is understood that compounds described herein may be substituted with esters, amides, and other hydrolyzable moieties according to the desire to make a prodrug with more desirable properties for percutaneous delivery as compared to the parent compound. For example, an ester form may penetrate the skin and/or partition in adipose tissue more effectively that the parent compound.

Methods of Treatment

As generally described herein, provided is a method for increasing fat locally in a body of a subject in need thereof, the method comprising percutaneously delivering to the subcutaneous fat of the subject a thiazolidinedione or an orexigenic compound, or a pharmaceutically acceptable salt or prodrug thereof. Delivering and administering are used interchangeably herein.

In certain embodiments, the delivering step comprises topical application to the skin, or by intradermal injection, subcutaneous injection, intramuscular injection, intralesional injection, transmucosal injection, or mucosal application.

In certain embodiments, percutaneously delivering comprises applying to the skin a pharmaceutical composition comprising a thiazolidinedione or an orexigenic compound, or a pharmaceutically acceptable salt or prodrug thereof, and a percutaneous carrier.

In other embodiments, percutaneously delivering comprises administering a pharmaceutical composition comprising a thiazolidinedione or an orexigenic compound, or a pharmaceutically acceptable salt or prodrug thereof, and a percutaneous carrier, by intradermal injection, subcutaneous injection, intramuscular injection, intralesional injection, transmucosal injection, or mucosal application.

In certain embodiments, the increasing fat locally in a body of a subject results in an increase in subcutaneous fat thickness at the treated site on a subject (e.g., at least a 10%, at least a 20%, at least a 30%, or at least a 40% increase in subcutaneous fat thickness) compared to a control site on the subject, or compared to the baseline (pre-administration) subcutaneous fat measurement, e.g., between 10% to 100%, increase, inclusive. In certain embodiments, the increasing is at least 10% greater at the treatment site than at a control site or compared to the baseline measurement. In certain embodiments, the increasing is at least 20% greater at the treatment site than at a control site or compared to the baseline measurement. In certain embodiments, the increasing is at least 30% greater at the treatment site than at a control site or compared to the baseline measurement. In certain embodiments, the increasing is at least 40% greater at the treatment site than at a control site or compared to the baseline measurement.

In some embodiments, the subject suffers from a subcutaneous fat deficiency, and the method is directed to treating the subcutaneous fat delivery.

In some embodiments, the subcutaneous fat deficiency is associated with a metabolic disorder. Exemplary metabolic disorders associated with subcutaneous fat deficiency include, but are not limited to, insulin resistance, diabetes (e.g., lipoatrophic diabetes), lipase deficiency, wasting, malnutrition, paraneoplastic condition, anorexia, pernicious anemia, celiac disease, and malabsorption syndrome.

In some embodiments, the subcutaneous fat deficiency is associated with an inflammatory condition. Exemplary inflammatory conditions associated with subcutaneous fat deficiency include, but are not limited to, complement component 3 (C3) deficiency, membranoproliferative glomerulonephritis, systemic lupus erythematosus, dermatomyositis, rheumatoid arthritis, temporal arteritis, and leukocytoclastic vasculitis.

In some embodiments, the subcutaneous fat deficiency is acquired. As used herein, "acquired" means a disorder that is not congenital. Exemplary conditions associated with acquired subcutaneous fat deficiency include, but are not limited to, HIV-associated lipodystrophy, lipidema, acquired partial lipodystrophy (Barraquer-Simons syndrome), acquired generalized lipodystrophy, Parry-Roberg syndrome, juvenile dermatomyositis, centrifugal abdominal lipodystrophy (lipodystrophia centrifugalis abdominalis infantilis), lipoatrophia annularis (Ferreira-Marques lipoatrophia), and localized lipodystrophy.

In some embodiments, the subcutaneous fat deficiency is congenital. Exemplary congenital conditions associated with subcutaneous fat deficiency include, but are not limited to, congenital generalized lipodystrophy (Beradinelli-Seip syndrome), familial partial dystrophy (e.g., Kobberling-type, Dunnigan type, or Type 3), Nakajo-Nishimura syndrome, Cockayne syndrome, SHORT syndrome, AREDYLD syndrome, mandibuloacral dysplasia, Keppen-Lubinsky syndrome, POEMS syndrome, Werner syndrome, Hutchinson-Gilford syndrome, and progeria.

In some embodiments, the subcutaneous fat deficiency is caused by a lipoatrophy-causing mutation in a gene selected from the group consisting of APLD, AKT2, C3, CAV1, CGL1 (AGPAT2), and CGL2 (BSCL2), LMF1, LMNA, PLIN1, PPARG, PSMB8, PTRF, and ZMPSTE24.

In some embodiments, the subcutaneous fat deficiency is caused by a medication. Exemplary medications known to cause subcutaneous fat deficiency include, but are not limited to, an antiretroviral (see, e.g., Domingo et al., AIDS Rev 2012; 14:112-123), an antibiotic (see, e.g., Kayikcioglu et al., J Pediatr 1996; 129:166-167), iron, a growth hormone, a detergent (see, e.g., U.S. Pat. No. 7,622,130), and a corticosteroid and/or a beta-adrenergic agonist (see, e.g, U.S. patent application Ser. No. 13/204,423). Exemplary antiretroviral medications are non-nucleoside reverse transcriptase inhibitors (e.g., efavirenz), nucleoside/nucleotide analog reverse transcriptase inhibitors (e.g., zidovudine), and HIV-1 protease inhibitors (e.g., nelfinavir). Exemplary corticosteroids include fluticasone, triamcinolone, betamethasone, prednisolone, methylprednisolone, and dexamethasone. Exemplary antibiotics include penicillin. An exemplary beta-adrenergic agonists is salmeterol. An exemplary detergent is deoxycholate.

In some embodiments, the subcutaneous fat deficiency is caused by surgery. For example, thiazolidinediones and/or an orexigenic compounds, as described herein, may also be useful as an adjunct to any of various kinds of surgery, whether used in the pre-operative, peri-operative, or post-operative period.

In some embodiments, a loss or deficiency of fat is caused by an injury. In some embodiments, the injury is selected from the group consisting of mechanical injury, burn, cryoinjury, and radiation injury.

In some embodiments, the subject does not necessarily suffer from a deficiency of fat.

For example, in some embodiments, the subject suffers from wrinkles of the skin, e.g., the skin is affected by wrinkles, and the method is directed to treating the wrinkles, e.g., by minimizing the appearance of wrinkles.

In certain embodiments, the skin is on the face, forehead, periorbital region of the face, midface, cheeks, chin, lips, breast, limbs, hands, trunk, hips, or buttocks.

In other embodiments, the subject suffers from dissatisfaction with the size or contour of a body part, and the method is directed to modifying the contour of the body part. As used herein, "modifying the contour of a body part" refers to changing the shape of the body part, for example, by augmenting the whole body part, by augmenting one or more area of the body part, or by augmenting one or more areas neighboring the body part. For example, the contour of the cheeks could be modified by augmenting the cheeks as a whole, by selectively augmenting only a portion of the cheeks (e.g., the malar eminences). Selective augmentation of a particular area is obtained by selectively treating the particular area, as described herein. Exemplary body parts contemplated for modification include, for example, the head (e.g., face such as the forehead, forehead, periorbital region, cheeks, chin, lips, and other anterior structures from top of forehead to bottom of chin), breast, limbs, hands, trunk, hips, and buttocks. In some embodiments, the method further comprises modifying the contour of the face. In some embodiments, the method further comprises modifying the contour of the cheeks. In some embodiments, the method further comprises modifying the contour of the chin. In some embodiments, the method further comprises modifying the contour of the jaw. In some embodiments, the method further comprises modifying the contour of the lips. In some embodiments, the method further comprises modifying the contour of a breast or breasts. In some embodiments, the method further comprises modifying the contour of a limb or limbs. In some embodiments, the method further comprises modifying the contour of the hands. In some embodiments, the method further comprises modifying the contour of the hips. In some embodiments, the method further comprises modifying the contour of the buttocks.

In yet other embodiments, the subject has transplanted fat, and the method is directed to augmenting the transplanted fat.

In certain embodiments, the subject suffers from diabetes, HIV, familial lipodystrophy, or a subcutaneous fat deficiency Pharmaceutical and Cosmetic Compositions As generally described herein, provided are compositions for percutaneous administration comprising an active ingredient and a pharmaceutically acceptable carrier.

As used herein, a "composition" refers to a pharmaceutical composition (e.g., useful for treatment of a particular disease, disorder, or condition, such as diagnosed by a medical professional) or cosmetic composition (e.g., for beautification purposes). Carrier and excipient are used interchangeably herein. Furthermore, as used herein, an "active ingredient" refers to a thiazolidinedione and/or an orexigenic compound, as described herein. In certain embodiments, the active ingredient is provided in a therapeutically effective amount in the composition.

In certain embodiments, the pharmaceutically acceptable carrier comprises a percutaneous carrier, and in this instance, the pharmaceutically acceptable carrier as a whole is viewed as a percutaneous carrier. In certain embodiments, the composition comprises a percutaneous carrier. In certain embodiments, the composition comprises a carrier (optionally a percutaneous carrier) for intradermal injection, subcutaneous injection, intramuscular injection, intralesional injection, transmucosal injection, or mucosal application. In certain embodiments, the composition further comprises one or more fatty acids. In certain embodiments, the composition further comprises one or more organic alcohols. In certain embodiments, the composition further comprises a penetration enhancer.

Exemplary pharmaceutically acceptable carriers include any and all solvents or other liquid vehicles, dispersion or suspension aids, surface active agents, isotonic agents, thickening or emulsifying agents, preservatives, buffering agents, lubricants and the like, as suited to the particular mode of administration desired.

General considerations in the formulation and/or manufacture of compositions can be found, for example, in *Remington's Pharmaceutical Sciences*, Sixteenth Edition, E. W. Martin (Mack Publishing Co., Easton, Pa., 1980), and *Remington: The Science and Practice of Pharmacy*, 21$^{st}$ Edition (Lippincott Williams & Wilkins, 2005). See also Singh et al., Local deep tissue penetration of compounds after dermal application: structure-tissue penetration relationships. JPET (1996) 279:908-917.

Compositions described herein can be prepared by any method known in the art of pharmacology. In general, such preparatory methods include the steps of bringing the active ingredient into association with a carrier and/or one or more other accessory ingredients, and then, if necessary and/or desirable, shaping and/or packaging the product into a desired single- or multi-dose unit.

Compositions can be prepared, packaged, and/or sold in bulk, as a single unit dose, and/or as a plurality of single unit doses. As used herein, a "unit dose" is discrete amount of the composition comprising a predetermined amount of the active ingredient. The amount of the active ingredient is generally equal to the dosage of the active ingredient which would be administered to a subject and/or a convenient fraction of such a dosage such as, for example, one-half or one-third of such a dosage.

Relative amounts of the active ingredient, the pharmaceutically acceptable carrier, and/or any additional ingredients in a composition will vary, depending upon the identity, size, and/or condition of the subject treated and further depending upon the route by which the composition is to be administered. By way of example, the composition may comprise between 0.1% and 100% (w/w) active ingredient.

Exemplary granulating and/or dispersing agents include potato starch, corn starch, tapioca starch, sodium starch glycolate, clays, alginic acid, guar gum, citrus pulp, agar, bentonite, cellulose and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, etc., and combinations thereof.

Exemplary surface active agents and/or emulsifiers include lipids/natural emulsifiers (e.g. acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g. bentonite [aluminum silicate] and Veegum [magnesium aluminum silicate]), long chain amino acid derivatives, high molecular weight alcohols (e.g. stearyl alcohol, cetyl alcohol, oleyl alcohol, triacetin monostearate, ethylene glycol distearate, glyceryl monostearate, and propylene glycol monostearate, polyvinyl alcohol), carbomers (e.g. carboxy polymethylene, polyacrylic acid, acrylic acid polymer, and carboxyvinyl polymer), carrageenan, cellulosic derivatives (e.g. carboxymethylcellulose sodium, powdered cellulose, hydroxymethyl cellulose, hydroxypropyl cellulose, hydroxypropyl methylcellulose, methylcellulose), sorbitan fatty acid esters (e.g. polyoxyethylene sorbitan monolaurate [Tween 20], polyoxyethylene sorbitan [Tween 60], polyoxyethylene sorbitan monooleate [Tween 80], sorbitan monopalmitate [Span 40], sorbitan monostearate [Span 60], sorbitan tristearate [Span 65], glyceryl monooleate, sorbitan monooleate [Span 80]), polyoxyethylene esters (e.g. polyoxyethylene monostearate [Myrj 45], polyoxyethylene hydrogenated castor oil, polyethoxylated castor oil, polyoxymethylene stearate, and Solutol), sucrose fatty acid esters, polyethylene glycol fatty acid esters (e.g. Cremophor), polyoxyethylene ethers, (e.g. polyoxyethylene lauryl ether [Brij 30]), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic F 68, Poloxamer 188, cetrimonium bromide, cetylpyridinium chloride, benzalkonium chloride, docusate sodium, etc. and/or combinations thereof.

Exemplary preservatives include antioxidants, chelating agents, antimicrobial preservatives, antifungal preservatives, alcohol preservatives, acidic preservatives, and other preservatives.

Exemplary antioxidants include alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite.

Exemplary chelating agents include ethylenediaminetetraacetic acid (EDTA) and salts and hydrates thereof (e.g., sodium edetate, disodium edetate, trisodium edetate, calcium disodium edetate, dipotassium edetate, and the like), citric acid and salts and hydrates thereof (e.g., citric acid monohydrate), fumaric acid and salts and hydrates thereof, malic acid and salts and hydrates thereof, phosphoric acid and salts and hydrates thereof, and tartaric acid and salts and hydrates thereof. Exemplary antimicrobial preservatives include benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal.

Exemplary antifungal preservatives include butyl paraben, methyl paraben, ethyl paraben, propyl paraben, benzoic acid, hydroxybenzoic acid, potassium benzoate, potassium sorbate, sodium benzoate, sodium propionate, and sorbic acid.

Exemplary alcohol preservatives include ethanol, polyethylene glycol, phenol, phenolic compounds, bisphenol, chlorobutanol, hydroxybenzoate, and phenylethyl alcohol.

Exemplary acidic preservatives include vitamin A, vitamin C, vitamin E, beta-carotene, citric acid, acetic acid, dehydroacetic acid, ascorbic acid, sorbic acid, and phytic acid.

Other preservatives include tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant Plus, Phenonip, methylparaben, Germall 115, Germaben II, Neolone, Kathon, and Euxyl. In certain embodiments, the preservative is an anti-oxidant. In other embodiments, the preservative is a chelating agent.

Exemplary buffering agents include citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, etc., and combinations thereof.

Exemplary lubricating agents include magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, etc., and combinations thereof.

Exemplary oils include almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, isopropyl myristate, jojoba, kukui nut, lavandin, lavender, lemon, litsea cubeba, macademia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and combinations thereof.

Injectable preparations, for example, sterile injectable aqueous or oleaginous suspensions can be formulated according to the known art using suitable dispersing or wetting agents and suspending agents. The sterile injectable preparation can be a sterile injectable solution, suspension or emulsion in a nontoxic parenterally acceptable diluent or solvent, for example, as a solution in 1,3-butanediol. Among the acceptable vehicles and solvents that can be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables. The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use. Suitable devices for injection, e.g., for intradermal injection, subcutaneous injection, intramuscular injection, intralesional injection, or transmucosal injection, of the active ingredient include short needle devices such as those described in U.S. Pat. Nos. 4,886,499; 5,190,521; 5,328,483; 5,527,288; 4,270,537; 5,015,235; 5,141,496; and 5,417,662. The active ingredient can be administered by devices which limit the effective penetration length of a needle into the skin, such as those described in PCT publication WO 99/34850 and functional equivalents thereof. Alternatively or additionally, conventional syringes can be used.

Dosage forms for topical administration (e.g., percutaneous administration to the skin, mucosal administration to the mucosa) of an active ingredient may include ointments, pastes, creams, lotions, gels, powders, ointment, paste, solutions, sprays, inhalants and/or patches. Such dosage forms can be prepared, for example, by dissolving and/or dispensing the active ingredient in the proper medium. Generally, the active ingredient is admixed under sterile conditions with a pharmaceutically acceptable carrier and/or any needed preservatives and/or buffers as can be required. Additionally, the present invention contemplates the use of patches, e.g., "percutaneous" patches, which often have the added advantage of providing controlled delivery of the active ingredient. Alternatively or additionally, the rate can be controlled by either providing a rate controlling membrane and/or by dispersing the active ingredient in a polymer matrix and/or gel.

An exemplary percutaneous patch contemplated herein can be made by combining the active ingredient and percutaneous carrier with an adhesive, and applying a layer of the combined active ingredient/carrier/adhesive to a solid matrix, e.g, a fabric mesh or plastic sheet. Methods for making transdermal patches are known in the art (see, e.g., Williams A C. Transdermal and Topical Drug Delivery, London: Pharmaceutical Press, 2003) and can be adapted for percutaneous delivery, with the proviso that the carrier and active ingredient concentration are adapted for percutaneous rather than transdermal delivery, as defined herein.

A percutaneous carrier is a pharmaceutically acceptable carrier adapted to deliver an active ingredient percutaneously, e.g., to subcutaneous fat. See, for example, Singh et al., Local deep tissue penetration of compounds after dermal application: structure-tissue penetration relationships. JPET (1996) 279:908-917. An exemplary percutaneous carrier in a marketed medication (Pennsaid® [diclofenac 1.5% topical solution]) is an aqueous solution comprising about 45% w/w dimethyl sulfoxide, with lesser amounts of propylene glycol, alcohol, and glycerin). Other exemplary percutaneous carriers include, but are not limited to, Lipoderm®, Vanpen®, HRT base, Occlusaderm®, and a Pluronic® lecithin organogel. See, e.g., Kumar et al., AAPS PharmSciTech (2005) 6:E298-E310. See also Examples 1-11 providing working examples of percutaneous carriers.

In certain embodiments, the percutaneous carrier (or composition) comprises one or more fatty acids. In some embodiments, the final concentration of the one or more fatty acids is between about 1 percent to about 20 percent by weight, inclusive. In some embodiments, the final concentration of the one or more fatty acids is between about 5 and about 15 percent, about 1 and about 10 percent, about 1 and about 2 percent, about 1 and about 3 percent, about 1 and about 5 percent, about 2 and about 4 percent, about 3 and about 5 percent, about 3 and about 7 percent, about 4 and about 6 percent, about 5 and about 7 percent, about 6 and about 8 percent, about 7 and about 10 percent, about 10 and about 20 percent, about 10 and about 15 percent, or about 15 and about 20 percent. In certain embodiments, the final concentration of the one or more fatty acids in the composition is 1, 2, 3, 4, 5, 6, 7, 8, 9, 10, 11, 12, 13, 14, 15, 16, 17, 18, 19, or 20 percent by weight.

In certain embodiments, the percutaneous carrier comprises the fatty acid oleic acid. However, the skilled artisan will appreciate that oleic acid can be substituted by one or more fatty acids of similar structure, e.g., wherein the acyl moiety of the fatty acid ($R^{FA1}$) is optionally substituted $C_{10}$-$C_{20}$ alkyl or optionally substituted $C_{10}$-$C_{20}$ alkenyl.

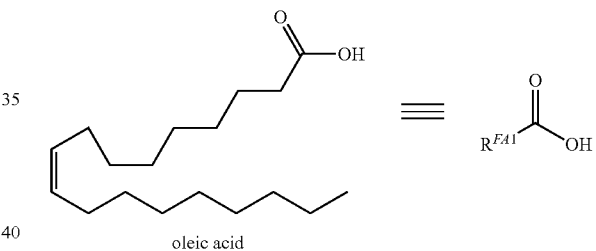

oleic acid

In certain embodiments, $R^{FA1}$ is an optionally substituted $C_{10}$-$C_{19}$ alkyl, $C_{10}$-$C_{18}$ alkyl, $C_{10}$-$C_{17}$ alkyl, $C_{10}$-$C_{16}$ alkyl, $C_{10}$-$C_{15}$ alkyl, $C_{10}$-$C_{14}$ alkyl, $C_{10}$-$C_{13}$ alkyl, $C_{11}$-$C_{20}$ alkyl, $C_{11}$-$C_{19}$ alkyl, $C_{11}$-$C_{18}$ alkyl, $C_{11}$-$C_{17}$ alkyl, $C_{11}$-$C_{16}$ alkyl, $C_{11}$-$C_{15}$ alkyl, $C_{11}$-$C_{14}$ alkyl, $C_{11}$-$C_{13}$ alkyl, $C_{12}$-$C_{19}$ alkyl, $C_{12}$-$C_{18}$ alkyl, $C_{12}$-$C_{17}$ alkyl, $C_{12}$-$C_{16}$ alkyl, $C_{12}$-$C_{15}$ alkyl, $C_{12}$-$C_{14}$ alkyl, $C_{12}$-$C_{13}$ alkyl, $C_{13}$-$C_{20}$ alkyl, $C_{13}$-$C_{19}$ alkyl, $C_{13}$-$C_{18}$ alkyl, $C_{13}$-$C_{17}$ alkyl, $C_{13}$-$C_{16}$ alkyl, $C_{13}$-$C_{15}$ alkyl, $C_{13}$-$C_{14}$ alkyl, $C_{14}$-$C_{20}$ alkyl, $C_{14}$-$C_{19}$ alkyl, $C_{14}$-$C_{18}$ alkyl, $C_{14}$-$C_{17}$ alkyl, $C_{14}$-$C_{16}$ alkyl, $C_{14}$-$C_{15}$ alkyl, $C_{15}$-$C_{20}$ alkyl, $C_{15}$-$C_{19}$ alkyl, $C_{15}$-$C_{18}$ alkyl, $C_{15}$-$C_{17}$ alkyl, or $C_{15}$-$C_{16}$ alkyl. In certain embodiments, $R^{FA1}$ is a straight chain (unbranched) alkyl group. In certain embodiments, $R^{FA1}$ is an unsubstituted alkyl group, i.e., comprising only carbon and hydrogen atoms. In certain embodiments, $R^{FA1}$ is a substituted alkyl group, e.g., substituted by halogen atoms.

In certain embodiments, $R^{FA1}$ is an optionally substituted $C_{10}$-$C_{19}$ alkenyl, $C_{10}$-$C_{18}$ alkenyl, $C_{10}$-$C_{17}$ alkenyl, $C_{10}$-$C_{16}$ alkenyl, $C_{10}$-$C_{15}$ alkenyl, $C_{10}$-$C_{14}$ alkenyl, $C_{10}$-$C_{13}$ alkenyl, $C_{11}$-$C_{20}$ alkenyl, $C_{11}$-$C_{19}$ alkenyl, $C_{11}$-$C_{18}$ alkenyl, $C_{11}$-$C_{17}$ alkenyl, $C_{11}$-$C_{16}$ alkenyl, $C_{11}$-$C_{15}$ alkenyl, $C_{11}$-$C_{14}$ alkenyl, $C_{11}$-$C_{13}$ alkenyl, $C_{12}$-$C_{19}$ alkenyl, $C_{12}$-$C_{18}$ alkenyl, $C_{12}$-$C_{17}$ alkenyl, $C_{12}$-$C_{16}$ alkenyl, $C_{12}$-$C_{15}$ alkenyl, $C_{12}$-$C_{14}$ alkenyl, $C_{12}$-$C_{13}$ alkenyl, $C_{13}$-$C_{20}$ alkenyl, $C_{13}$-$C_{19}$ alkenyl, $C_{13}$-$C_{18}$ alkenyl, $C_{13}$-$C_{17}$ alkenyl, $C_{13}$-$C_{16}$ alkenyl, $C_{13}$-$C_{15}$ alkenyl, $C_{13}$-$C_{14}$ alkenyl, $C_{14}$-$C_{20}$ alkenyl, $C_{14}$-$C_{19}$ alkenyl, $C_{14}$-$C_{18}$ alkenyl, $C_{14}$-$C_{17}$ alkenyl, $C_{14}$-$C_{16}$ alkenyl, $C_{14}$-$C_{15}$ alkenyl, $C_{15}$-$C_{20}$ alkenyl, $C_{15}$-$C_{19}$ alkenyl, $C_{15}$-$C_{18}$ alkenyl, $C_{15}$-$C_{17}$ alkenyl, $C_{15}$-$C_{16}$ alkenyl. In certain embodiments, $R^{FA1}$ is a unbranched alkenyl group. In certain embodiments, $R^{FA1}$ is an unsubstituted alkenyl group, i.e., comprising only carbon and hydrogen atoms. In certain embodiments, $R^{FA1}$ is a substituted alkenyl group, e.g., substituted by halogen atoms. In certain embodiments, $R^{FA1}$ is an alkenyl group comprising 1, 2, 3, or 4 double bonds, each independently cis or trans.

In certain embodiments, $R^{FA1}$ is an alkenyl group comprising at least one cis double bond, e.g., 1, 2, 3, or 4 cis double bonds. In certain embodiments, $R^{FA1}$ is an alkenyl group of formula (a):

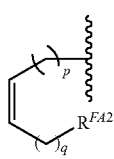

(a)

wherein:
  p is an integer between 2 and 8, inclusive;
  q is an integer between 1 and 8, inclusive; and
  $R^{FA2}$ is an optionally substituted $C_1$-$C_{10}$ alkyl, or an optionally substituted $C_2$-$C_{10}$ alkenyl, provided the sum of carbons of formula (a) does not exceed 20.

In certain embodiments, $R^{FA2}$ is an optionally substituted $C_1$-$C_9$ alkyl, $C_1$-$C_8$ alkyl, $C_1$-$C_7$ alkyl, $C_1$-$C_6$ alkyl, $C_1$-$C_5$ alkyl, $C_1$-$C_4$ alkyl, $C_1$-$C_3$ alkyl, $C_1$-$C_2$ alkyl, $C_2$-$C_{10}$ alkyl, $C_2$-$C_9$ alkyl, $C_2$-$C_8$ alkyl, $C_2$-$C_7$ alkyl, $C_2$-$C_6$ alkyl, $C_2$-$C_5$ alkyl, $C_2$-$C_4$ alkyl, $C_2$-$C_3$ alkyl, $C_3$-$C_{10}$ alkyl, $C_3$-$C_9$ alkyl, $C_3$-$C_8$ alkyl, $C_3$-$C_7$ alkyl, $C_3$-$C_6$ alkyl, $C_3$-$C_5$ alkyl, $C_3$-$C_4$ alkyl, $C_4$-$C_{10}$ alkyl, $C_4$-$C_9$ alkyl, $C_4$-$C_8$ alkyl, $C_4$-$C_7$ alkyl, $C_4$-$C_6$ alkyl, $C_4$-$C_5$ alkyl, $C_5$-$C_{10}$ alkyl, $C_5$-$C_9$ alkyl, $C_5$-$C_8$ alkyl, $C_5$-$C_7$ alkyl, $C_5$-$C_6$ alkyl, $C_6$-$C_{10}$ alkyl, $C_6$-$C_9$ alkyl, $C_6$-$C_8$ alkyl, $C_6$-$C_7$ alkyl, $C_7$-$C_{10}$ alkyl, $C_7$-$C_9$ alkyl, $C_7$-$C_8$ alkyl, $C_8$-$C_{10}$ alkyl, $C_8$-$C_9$ alkyl, or $C_9$-$C_{10}$ alkyl. In certain embodiments, $R^{FA2}$ is a straight chain (unbranched) alkyl group. In certain embodiments, $R^{FA2}$ is an unsubstituted alkyl group, i.e., comprising only carbon and hydrogen atoms. In certain embodiments, $R^{FA2}$ is a substituted alkyl group, e.g., substituted by halogen atoms.

In certain embodiments, $R^{FA2}$ is an optionally substituted $C_2$-$C_9$ alkenyl, $C_2$-$C_8$ alkenyl, $C_2$-$C_7$ alkenyl, $C_2$-$C_6$ alkenyl, $C_2$-$C_5$ alkenyl, $C_2$-$C_4$ alkenyl, $C_2$-$C_3$ alkenyl, $C_3$-$C_{10}$ alkenyl, $C_3$-$C_9$ alkenyl, $C_3$-$C_8$ alkenyl, $C_3$-$C_7$ alkenyl, $C_3$-$C_6$ alkenyl, $C_3$-$C_5$ alkenyl, $C_3$-$C_4$ alkenyl, $C_4$-$C_{10}$ alkenyl, $C_4$-$C_9$ alkenyl, $C_4$-$C_8$ alkenyl, $C_4$-$C_7$ alkenyl, $C_4$-$C_6$ alkenyl, $C_4$-$C_5$ alkenyl, $C_5$-$C_{10}$ alkenyl, $C_5$-$C_9$ alkenyl, $C_5$-$C_8$ alkenyl, $C_5$-$C_7$ alkenyl, $C_5$-$C_6$ alkenyl, $C_6$-$C_{10}$ alkenyl, $C_6$-$C_9$ alkenyl, $C_6$-$C_8$ alkenyl, $C_6$-$C_7$ alkenyl, $C_7$-$C_{10}$ alkenyl, $C_7$-$C_9$ alkenyl, $C_7$-$C_8$ alkenyl, $C_8$-$C_{10}$ alkenyl, $C_8$-$C_9$ alkenyl, or $C_9$-$C_{10}$ alkenyl. In certain embodiments, $R^{FA2}$ is a straight chain (unbranched) alkenyl group. In certain embodiments, $R^{FA2}$ is an unsubstituted alkenyl group, i.e., comprising only carbon and hydrogen atoms. In certain embodiments, $R^{FA2}$ is a substituted alkenyl group, e.g., substituted by halogen atoms. In certain embodiments, $R^{FA2}$ is a substituted alkenyl group, e.g., substituted by halogen atoms. In certain embodiments, $R^{FA2}$ is an alkenyl group comprising 1 or 2 double bonds, each independently cis or trans.

In certain embodiments, $R^{FA1}$ is selected from any one of the following saturated or unsaturated fatty acyl moieties:

| | |
|---|---|
| Lauric | —$(CH_2)_{10}CH_3$ (11 aliphatic carbons), |
| Myristic | —$(CH_2)_{12}CH_3$ (13 aliphatic carbons), |
| Palmitic | —$(CH_2)_{14}CH_3$ (15 aliphatic carbons), |
| Stearic | —$(CH_2)_{16}CH_3$ (17 aliphatic carbons), |
| Myristoleic | —$(CH_2)_7CH\!\!=\!\!CH(CH_2)_3CH_3$, | i.e., of formula

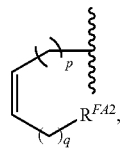

wherein p=7, q=3, $R^{FA2}$=—$CH_3$ (13 aliphatic carbons)
Palmitoliec* —$(CH_2)_7CH\!\!=\!\!CH(CH_2)_5CH_3$,
  i.e., of formula

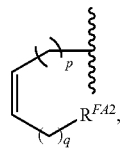

wherein p=7, q=5, $R^{FA2}$=—$CH_3$ (15 aliphatic carbons)
Sapienic* —$(CH_2)_4CH\!\!=\!\!CH(CH_2)_8CH_3$,
  i.e., of formula

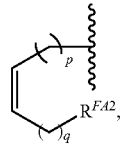

wherein p=4, q=8, $R^{FA2}$=—$CH_3$ (15 aliphatic carbons)
Oleic —$(CH_2)_7CH\!\!=\!\!CH(CH_2)_7CH_3$,
  i.e., of formula

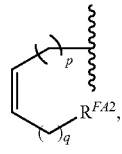

wherein p=7, q=7, $R^{FA2}$=—$CH_3$ (17 aliphatic carbons)
Linoleic* —$(CH_2)_7CH\!\!=\!\!CHCH_2CH\!\!=\!\!CH(CH_2)_4CH_3$, i.e., of formula

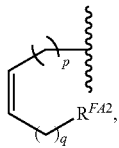

wherein p=7, q=1, $R^{FA2}$=$C_7$-alkenyl (17 aliphatic carbons)

α-Linolenic** —$(CH_2)_7$
CH=CHCH$_2$CH=CHCH$_2$CH=CHCH$_2$CH$_3$
i.e., of formula

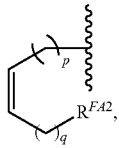

wherein p=7, q=1, $R^{FA2}$=$C_7$-alkenyl (17 aliphatic carbons)

In some embodiments, the percutaneous carrier (or composition) comprises one or more organic alcohols, e.g., $R^{aa}$—OH, wherein $R^{aa}$ is as defined herein. In certain embodiments, $R^{aa}$ is $C_{1-10}$ alkyl, $C_{1-10}$ perhaloalkyl, $C_{2-10}$ alkenyl, $C_{2-10}$ alkynyl, hetero$C_{1-10}$ alkyl, hetero$C_{2-10}$ alkenyl, or hetero$C_{2-10}$alkynyl, wherein each alkyl, alkenyl, alkynyl, heteroalkyl, heteroalkenyl, and heteroalkynyl is independently substituted with 0, 1, 2, 3, 4, or 5 $R^{dd}$ groups, as defined herein (e.g., substituted by —OH or —$OR^{ee}$, as defined herein). In certain embodiments, $R^{aa}$ is $C_{1-10}$ alkyl, e.g., $C_{1-9}$ alkyl, $C_{1-8}$alkyl, $C_{1-6}$ alkyl, $C_{1-4}$ alkyl, $C_{1-3}$ alkyl, $C_{1-2}$ alkyl, $C_{2-10}$ alkyl, $C_{2-9}$ alkyl, $C_{2-8}$ alkyl, $C_{2-6}$ alkyl, $C_{2-4}$ alkyl, or $C_{2-3}$ alkyl. In certain embodiments, $R^{aa}$ is an unsubstituted alkyl group. In certain embodiments, Raa is a substituted alkyl group, e.g., substituted with 1, 2, 3, 4, or 5 $R^{dd}$ groups, as defined herein (e.g., substituted by —OH or —$OR^{ee}$, as defined herein). Exemplary organic alcohols include, but are not limited to, methanol, ethanol, propanol, isopropanol, 1,3-butanediol, propylene glycol, or ethylene glycol. In certain embodiments, the percutaneous carrier comprises propylene glycol and/or ethanol. In some embodiments, the final concentration of the one or more organic alcohols in the composition is between about 5 percent and about 99 percent by weight, inclusive.

In some embodiments, the percutaneous carrier (or composition) comprises one or more organic alcohols which acts as a base excipient (i.e., constituting the major component of the composition). In some embodiments, the final concentration of the organic alcohol base excipient in the composition is greater than 50 percent and about 99 percent by weight, inclusive. In some embodiments, the final concentration of the organic alcohol base excipient in the composition is between about 51 percent and 60 percent, 51 percent and about 70 percent, about 60 percent and about 70 percent, about 60 percent and about 80 percent, about 70 percent and about 80 percent, about 70 percent and about 90 percent, about 80 percent and about 90 percent, about 85 percent and about 95 percent, about 90 percent and about 95 percent, about 90 percent and about 99 percent, and about 95 percent and about 99 percent, inclusive. In certain embodiments, the organic alcohol which acts as a base excipient is ethanol.

In some embodiments, the percutaneous carrier (or composition) comprises one or more organic alcohols which is not the base component of the composition (e.g., provided as a component in 50% or less by weight). In certain embodiments, the final concentration of the organic alcohol in the composition is between about 5 percent and about 50 percent by weight, inclusive. In some embodiments, the final concentration of the organic alcohol is between about 5 percent and 10 percent, about 5 percent and about 15 percent, about 10 percent and about 15 percent, about 10 percent and about 20 percent, about 10 percent and about 30 percent, about 10 percent and about 40 percent, about 15 percent and about 20 percent, about 15 percent and about 25 percent, about 20 percent and about 25 percent, about 20 percent and about 30 percent, about 25 percent and about 30 percent, about 25 percent and about 35 percent, about 30 percent and about 35 percent, about 30 percent and about 40 percent, about 35 percent and about 40 percent, about 35 percent and about 45 percent, about 40 percent and about 45 percent, about 40 percent and about 50 percent, about 40 percent and about 45 percent, or about 45 percent and about 50 percent, inclusive. In certain embodiments, the percutaneous carrier comprises an organic alcohol, wherein the organic alcohol is present in 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30% by weight in the composition. In certain embodiments, the organic alcohol that is not the base component of the composition is propylene glycol.

In certain embodiments, the percutaneous carrier (or composition) further comprises a penetration enhancer. A variety of penetration enhancers are known in the art, e.g., enzymes, lactams, propylene glycol, alcohols such as ethanol and propanol, polyols, limonene, terpenes, dioxolane, propylene glycol, ethylene glycol, other glycols, glycerol, sulfoxides such as dimethylsulfoxide (DMSO) and methyl dodecyl sulfoxide, esters such as isopropyl myristate/palmitate, ethyl acetate, butyl acetate, methyl propionate, and capric/caprylic triglycerides, ketones, such as 2-alkyl cyclohexanones, t-butyl cyclohexanones, and various $C_8$ derivatives; amides, such as acetamides; oleates, such as triolein; various surfactants, such as Brij 96, Tweens (Atlas Chemical Company), and sodium lauryl sulfate; various alkanoic acids such as caprylic acid; lacta compounds, such as Azone; alkanols, such as oleyl alcohol; and admixtures thereof. It is understood that a penetration enhancer does not interfere with the chemical stability or pharmacologic action of the active ingredient, or interact adversely with other components(s) of the formulation. In certain embodiments, the percutaneous carrier comprises between 40% and 99% w/w DMSO, useful as a penetration enhancer.

In some embodiments, the percutaneous carrier (or composition) further comprises a viscosity enhancing agent, also referred to as a gelling agent. A viscosity enhancing agent, as used herein, is a substance which increases the viscosity of a solution or liquid/solid mixture. Exemplary viscosity enhancing agents include, but are not limited to, glycerin; cellulose derivatives (e.g., methylcellulose (MC); hydroxypropylmethylcellulose (HPMC); carboxymethylcellulose (CMC); microcrystalline cellulose (CC); ethyl cellulose; hydroxyethyl cellulose (HEC); hydroxypropyl cellulose (HPC); cellulose); gelatin; starch; hetastarch; poloxamers; pluronics; sodium CMC; sorbitol; acacia; povidone; carbopol; polycarbophil; chitosan; alginate; chitosan glutamate; hyaluronic acid; elastin; hyaluronan; maltodextrin DE; deoxyglycocholate (GDC); polymethacrylic acid; glycols (e.g., polymethylene glycol; polyethylene glycol); cyclodextrins (e.g., sulfobutylether B cyclodextrin); sodium tauro-dihydrofusidate (STDHF); and N-trimethyl chitosan chloride (TMC). In certain embodiments, the viscosity enhancing agent is a cellulose derivative, e.g., hydroxypropyl cellulose (HPC). In certain embodiments, the composition comprises a viscosity enhancing agent in about 0.5% to about 5% by weight, inclusive, e.g., 0.5%, 0.6%, 0.7%, 0.8%, 0.9%, 1%, 2%, 3%, 4%, or 5% by weight. In certain embodiments, the composition comprises a viscosity enhancing agent in about 1% by weight.

In certain embodiment, the composition is a gel.

In certain embodiments, the composition further comprises an antioxidant, e.g., alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite, in between about 0.001% to about 0.1% by weight, inclusive; e.g., about 0.002%, about 0.004%, about 0.006%, about 0.008%, about 0.01%, about 0.02%, about 0.04%, about 0.06%, about 0.08%, or about 0.1% by weight. In certain embodiments, the composition comprises an antioxidant in about 0.002% by weight.

In certain embodiments, the composition is anhydrous, and contains between 0% and about 1% by weight of water, inclusive. However, in certain embodiments, the composition does comprise water; e.g., for example, water is added to the composition and comprises greater than 1% of water. In certain embodiments, the composition comprises between about 5% to about 30% by weight, inclusive, of water, e.g., between about 10% to about 25% by weight of water, inclusive.

Although the descriptions of compositions provided herein are principally directed to compositions which are suitable for administration to humans, it will be understood by the skilled artisan that such compositions are generally suitable for administration to animals of all sorts. Modification of compositions suitable for administration to humans in order to render the compositions suitable for administration to various animals is well understood, and the ordinarily skilled veterinary pharmacologist can design and/or perform such modification with ordinary experimentation. General considerations in the formulation and/or manufacture of compositions can be found, for example, in Remington: The Science and Practice of Pharmacy 21st ed., Lippincott Williams & Wilkins, 2005.

Still further encompassed by the invention are pharmaceutical or cosmetic packs and/or kits. Pharmaceutical or cosmetic packs and/or kits provided may comprise a provided composition (i.e., a pharmaceutical or cosmetic composition) and a container (e.g., a vial, ampoule, bottle, syringe, and/or dispenser package, or other suitable container). In some embodiments, provided kits may optionally further include a second container comprising a suitable aqueous carrier for dilution or suspension of the provided composition for preparation of administration to a subject. In some embodiments, contents of provided formulation container and solvent container combine to form at least one unit dosage form.

The active ingredient can be administered using any amount and any local route of administration effective for treatment. The exact amount required will vary from subject to subject, depending on the species, age, and general condition of the subject, the severity of the infection, the particular composition, its mode of administration, its mode of activity, and the like.

The active ingredient is typically formulated in dosage unit form for ease of administration and uniformity of dosage. It will be understood, however, that the total daily usage of the compositions of the present invention will be decided by the attending physician within the scope of sound medical judgment. The specific therapeutically effective dose level for any particular subject will depend upon a variety of factors including the condition being treated and the severity of the condition; the activity of the specific active ingredient employed; the specific composition employed; the age, body weight, general health, sex and diet of the subject; the time of administration, route of administration, and rate of excretion of the specific active ingredient employed; the duration of the treatment; drugs used in combination or coincidental with the specific active ingredient employed; and like factors well known in the medical arts.

The desired dosage can be delivered three times a day, two times a day, once a day, every other day, every third day, every week, every two weeks, every three weeks, or every four weeks. In certain embodiments, the desired dosage can be delivered using multiple administrations (e.g., two, three, four, five, six, seven, eight, nine, ten, eleven, twelve, thirteen, fourteen, or more administrations). As demonstrated in the accompanying Examples, daily administration to the subject can be adequate (but not necessarily preferable) to achieve the desired effect. A daily administration schedule is considered convenient for human use. The active ingredient may be administered by the subject to himself or herself repeatedly and without special equipment or training, although a medical professional also can also administer the active ingredient to the subject.

In certain embodiments, a therapeutically effective amount of the active ingredient for administration one or more times a day to may comprise about 0.00001 mg to about 1000 mg per $cm^2$ of treated skin, about 0.0001 mg to about 1000 mg per $cm^2$, about 0.001 mg to about 1000 mg per $cm^2$, about 0.01 mg to about 1000 mg per $cm^2$, about 0.1 mg to about 1000 mg per $cm^2$, about 1 mg to about 1000 mg per $cm^2$, about 1 mg to about 100 mg per $cm^2$, about 1 mg to about 10 mg per $cm^2$, about 10 mg to about 1000 mg per $cm^2$, or about 100 mg to about 1000 mg per $cm^2$.

In certain percutaneous embodiments, the area of skin to be treated one or more times a day to may comprise about 1 $cm^2$ to about 10,000 $cm^2$, about 1 $cm^2$ to about 1,000 $cm^2$, about 1 $cm^2$ to about 100 $cm^2$, about 1 $cm^2$ to about 10 $cm^2$, about 10 $cm^2$ to about 100 $cm^2$, about 10 $cm^2$ to about 1,000 $cm^2$, about 100 $cm^2$ to about 1,000 $cm^2$, or about 1,000 $cm^2$ to about 10,000 $cm^2$, inclusive.

In certain embodiments, a therapeutically effective amount of the active ingredient for administration one or more times a day to a 70 kg adult human may comprise about 0.0001 mg to about 3000 mg, about 0.0001 mg to about 2000 mg, about 0.0001 mg to about 1000 mg, about 0.001 mg to about 1000 mg, about 0.01 mg to about 1000 mg, about 0.1 mg to about 1000 mg, about 1 mg to about 1000 mg, about 1 mg to about 100 mg, about 10 mg to about 1000 mg, or about 100 mg to about 1000 mg, inclusive, of the active ingredient per unit dosage form. It will be appreciated that dose ranges as described herein provide guidance for the administration of provided pharmaceutical compositions to an adult. The amount to be administered to, for example, a child or an adolescent can be determined by a medical practitioner or person skilled in the art and can be lower or the same as that administered to an adult.

In certain embodiments, the composition comprises between about 0.0001 percent to about 5 percent by weight, inclusive, of a thiazolidinedione or an orexigenic compound, or pharmaceutically acceptable salt or prodrug thereof, to the subject, e.g., between about 0.001 percent to about 2 percent by weight, between about 0.01 percent to about 2 percent by weight, between about 0.1 percent to about 2 percent by weight, between about 0.5 and about 2 percent by weight, between about 1 percent to about 3 percent by weight, or between about 3 and about 5 percent by weight, inclusive.

In certain embodiments, the concentration of the thiazolidinedione is between about 0.001 percent to about 2 percent by weight, between about 0.01 percent to about 2 percent by weight, between about 0.1 percent to about 2 percent by weight, between about 0.5 and about 2 percent by weight, between about 1 percent to about 3 percent by weight, or between about 3 and about 5 percent by weight, inclusive.

In certain embodiments, the concentration of the orexigenic pregnane derivative is between about 0.001 percent to about 2 percent by weight, between about 0.01 percent to about 2 percent by weight, between about 0.1 percent to about 2 percent by weight, between about 0.5 and about 2 percent by weight, between about 1 percent to about 3 percent by weight, or between about 3 and about 5 percent by weight, inclusive.

Various compositions are further contemplated herein.

For example, in one exemplary embodiment, the composition comprises a thiazolidinedione or an orexigenic compound, or a pharmaceutically acceptable salt or prodrug thereof, and a percutaneous carrier comprising one or more fatty acids (e.g., oleic acid), wherein the fatty acid concentration is between about 1 and about 10 percent by weight, inclusive, in the composition. In certain embodiments, the percutaneous carrier further comprises one or more organic alcohols (e.g., propylene glycol and/or ethanol). In certain embodiments, the organic alcohol concentration is between about 5 percent and about 99 percent, inclusive, by weight in the composition. In certain embodiments, the composition comprises the thiazolidinedione or the orexigenic compound between about 0.1 percent and about 2 percent by weight, inclusive, in the composition. In certain embodiments, the composition further comprises a penetration enhancer. In certain embodiments, the composition further comprises a viscosity enhancing agent. In certain embodiments, the composition further comprises an antioxidant.

For example, in one exemplary embodiment, the composition comprises a thiazolidinedione or an orexigenic compound, or a pharmaceutically acceptable salt or prodrug thereof, and a percutaneous carrier comprising one or more organic alcohols (e.g., propylene glycol and/or ethanol), wherein the organic alcohol concentration is between about 5 percent and about 99 percent, inclusive, by weight in the composition. In certain embodiments, the composition further comprises one or more fatty acids (e.g., oleic acid), wherein the fatty acid concentration is between about 1 and about 10 percent by weight, inclusive, in the composition. In certain embodiments, the composition comprises the thiazolidinedione or the orexigenic compound between about 0.1 percent and about 2 percent by weight, inclusive, in the composition. In certain embodiments, the composition further comprises a penetration enhancer. In certain embodiments, the composition further comprises a viscosity enhancing agent. In certain embodiments, the composition further comprises an antioxidant.

In another exemplary embodiment, the composition comprises a thiazolidinedione or an orexigenic compound, or a pharmaceutically acceptable salt or prodrug thereof, about 0.1 percent and about 2 percent by weight, inclusive, and a percutaneous carrier comprising one or more fatty acids (e.g., oleic acid), propylene glycol and ethanol, wherein the concentration of the fatty acid is between about 1 and about 10 percent by weight, inclusive, the concentration of the propylene glycol is between about 10 and about 40 percent by weight, inclusive, and the concentration of the ethanol is between about 50 and about 90 percent by weight, inclusive, in the composition. In certain embodiments, the composition further comprises a viscosity enhancing agent at about 0.5 to about 2 percent by weight, inclusive. In certain embodiments, the composition further comprises an antioxidant.

In another exemplary embodiment, the composition comprises a thiazolidinedione or an orexigenic compound, or a pharmaceutically acceptable salt or prodrug thereof, between about 0.1 percent and about 1 percent by weight, inclusive, and a percutaneous carrier comprising a fatty acid (e.g., oleic acid), propylene glycol, and ethanol, wherein the concentration of the fatty acid is between about 1 to about 5 percent by weight, inclusive, the concentration of the propylene glycol is between about 20 and about 40 percent by weight, inclusive, and the concentration of the ethanol is between about 60 and about 80 percent by weight, inclusive, in the composition. In certain embodiments, the composition further comprises a viscosity enhancing agent at about 0.5 to about 2 percent by weight, inclusive. In certain embodiments, the composition further comprises an antioxidant.

In yet another exemplary embodiment, the composition comprises a thiazolidinedione or an orexigenic compound, or a pharmaceutically acceptable salt or prodrug thereof, between about 0.1 percent and about 5 percent by weight, inclusive, and a percutaneous carrier comprising oleic acid, propylene glycol, and ethanol, wherein the concentration of the oleic acid is about 3 percent by weight, inclusive, the concentration of the propylene glycol is about 27 percent by weight, inclusive, and the concentration of the ethanol is about 65 to about 70 percent by weight, inclusive. In certain embodiments, the composition further comprises a viscosity enhancing agent at about 0.5 to about 2 percent by weight, inclusive. In certain embodiments, the composition further comprises an antioxidant.

In yet another exemplary embodiment, the composition comprises a thiazolidinedione or an orexigenic compound, or a pharmaceutically acceptable salt or prodrug thereof, between about 0.1 percent and about 5 percent by weight, inclusive, and a percutaneous carrier comprising oleic acid, propylene glycol, and ethanol, wherein the concentration of the oleic acid is about 3 percent by weight, the concentration of the propylene glycol is about 27 percent by weight, and the concentration of the ethanol is about 40 to about 60 percent by weight, inclusive. In certain embodiments, the composition further comprises a viscosity enhancing agent at about 0.5 to about 2 percent by weight, inclusive. In certain embodiments, the composition further comprises an antioxidant.

It will be also appreciated that the active ingredient can be administered in combination with one or more additional therapeutically active agents ("agents" or "active agents"). The compound or composition can be administered concurrently with, prior to, or subsequent to, one or more additional agents. In general, the active ingredient and each additional active agent will be administered at a dose and/or on a time schedule determined for the ingredient and agent. In will further be appreciated that the active ingredient and active agent utilized in this combination can be administered together in a single composition or administered separately in different compositions. The particular combination to employ in a regimen will take into account compatibility of the active ingredient with the active agent and/or the desired therapeutic effect to be achieved. In general, it is expected that additional active agents utilized in combination be utilized at levels that do not exceed the levels at which they are utilized individually. In some embodiments, the levels utilized in combination will be lower than those utilized individually. The active ingredient can be administered in combination with an active agent that improves bioavailability, reduces and/or modifies metabolism, inhibits excretion, and/or modifies distribution within the body. It will also be appreciated that therapy employed may achieve a desired effect for the same disorder, and/or it may achieve different effects.

EXAMPLES

In light of the foregoing description, the specific non-limiting examples presented below are for illustrative purposes and not intended to limit the scope of the invention in any way.

Example 1

A randomized controlled trial was conducted on C57BL/6J. Male mice approximately six weeks old were prospectively randomized into groups and assigned to the following treatment conditions (n=5 animals per group):

TABLE 1

| Group | Compound | Class | Formulation | Dose |
|---|---|---|---|---|
| 1 | Vehicle | Placebo | Lipoderm | 0.1 cc to flank, daily |
| 2 | Pioglitazone | Thiazolidinedione (PPARγ activator) | 5 mM in Lipoderm | 0.1 cc to flank, daily |
| 3 | Harmine | β-carboline alkaloid (PPARγ activator) | 5 mM in Lipoderm | 0.1 cc to flank, daily |
| 4 | Megestrol acetate | Progesterone analog | 5 mM in Lipoderm | 0.1 cc to flank, daily |
| 5 | Efavirenz | Non-nucleoside reverse transcriptase inhibitor | 5 mM in Lipoderm | 0.1 cc to flank, daily |

Animals were shaved and depilated over the flanks at the start of the study.

Animals were kept in identical conditions and fed ab libitum with a standardized high-fat diet (70% kcal fat). Animals were weighed three times weekly. Following 24 consecutive days of treatment, mice were sacrificed and samples of skin and adjacent fat from the treated flanks are taken for histologic examination.

Table 2 summarizes mean weight gain by group from Day 0 until Day 24. Compared to mice the vehicle group, those in Group 2 (pioglitazone) and Group 4 (megestrol acetate) were associated with numerically higher weight gain.

TABLE 2

| Group | Compound | Class | Mean weight gain | Relative to vehicle |
|---|---|---|---|---|
| 1 | Vehicle | Placebo | 6.7 g | |
| 2 | Pioglitazone | Thiazolidinedione (PPARγ activator) | 7.4 g | 112% |
| 3 | Harmine | β-carboline alkaloid (PPARγ activator) | 6.8 g | 102% |
| 4 | Megestrol acetate | Progesterone analog | 8.0 g | 120% |
| 5 | Efavirenz | Non-nucleoside reverse transcriptase inhibitor | 6.1 g | 92% |

Figure 2:
FIG. 2 is a photograph of a representative mouse following 24 days of treatment with percutaneous megestrol, as further described in Example 1. The photograph is oriented such that the left flank of the animal is shown at left. Skin folds on the left (untreated) and right (treated) flanks are compared, with the approximate thickness indicated by a yellow line. Thickness of the skin fold at left was about 2 mm, whereas the skin fold at right was about 4 mm.

Animals were examined on Day 24 with attention to relative skin fold thickness of the left and right flanks. Animals in Groups 1, 3, and 5 appeared symmetric. Animals in Group 2 (pioglitazone) and Group 4 (megestrol acetate) were asymmetric, with thicker skin folds on the treated flanks compared to the untreated flanks. A representative view of the asymmetry seen in Groups 2 and 4 is shown in FIG. 1. The skin fold on the right (treated) flank of the animal was markedly thicker (about 4 mm) than the skin fold on the left (untreated) flank (about 2 mm). As shown in FIG. 2, the gross difference in skin fold thickness was accounted for by a difference in the thickness of subcutaneous fat, with thicker fat on the right (treated) flank versus the left (untreated) flank.

Example 2

Figure 3:
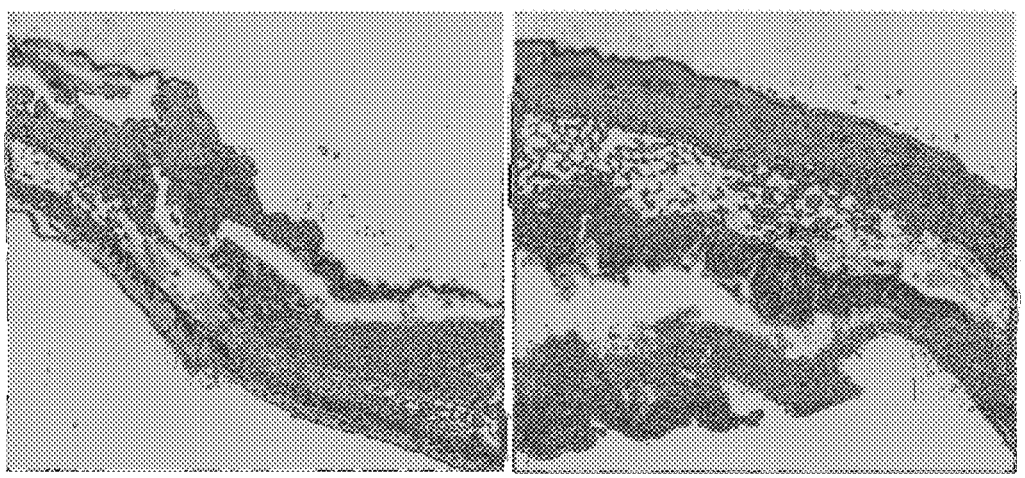
FIG. 3 shows photomicrographs of hematoxylin- and eosin-stained axial sections of tissue from the left and right flanks shown in FIG. 2. Subcutaneous fat was thicker on the right (treated) flank (right panel) compared to the left (untreated) flank (left panel). Both panels shown at same magnification.
Figure 4:
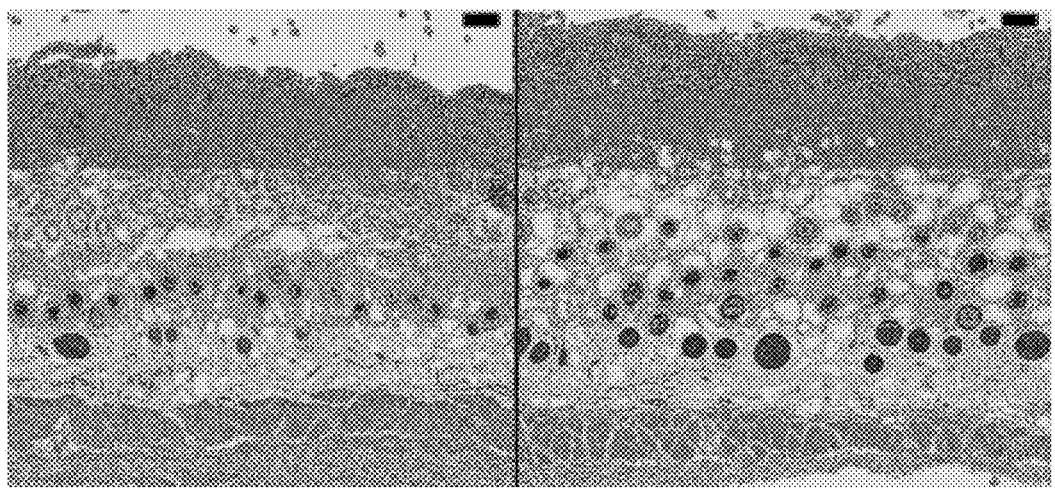
FIG. 4 shows photomicrographs of hematoxylin- and eosin-stained axial sections of tissue from the right flanks of representative mice treated with vehicle (left panel) or percutaneous rosiglitazone (right panel). Compared to mice treated with vehicle (left panel), subcutaneous fat was thicker on the flanks of animals treated with rosiglitazone (right panel). Both panels shown at same magnification.

A separate study was performed according to the methods in Example 1, wherein groups of animals were treated with vehicle, rosiglitazone 0.1%, or rosiglitazone 0.3% by weight. No adverse effects were noted. Skin and subcutaneous tissue and muscle were collected at the end of the study, fixed in formalin, stained with hematoxylin and eosin, examined microscopically, and measured digitally. Table 3 presents the absolute and relative thicknesses of subcutaneous fat by treatment group, as well as the relative increase in body mass. FIG. 3 show representative micrographs of tissue from animals treated with vehicle and rosiglitazone 0.3%. The micrographs showed a selective local increase in the thickness of subcutaneous fat. No adverse effect, such as inflammation was seen.

TABLE 3

| Compound | Mean Adipose Thickness (mm) ± SEM | Relative to Vehicle (%) | Increase in body mass (%) |
|---|---|---|---|
| Vehicle | 0.295 ± 0.066 | 100% | 6.6% |
| Rosiglitazone 0.1% | 0.472 ± 0.058 | 160%* | 5.8% |
| Rosiglitazone 0.3% | 0.562 ± 0.089 | 190%* | 8.9% |

Thus, in a prospective randomized trial in mice, percutaneous rosiglitazone was well tolerated caused a dose-dependent, local increase in subcutaneous fat without a systemic effect.

Example 3

A composition for locally increasing subcutaneous fat was prepared as follows:

TABLE 4

| Ingredients per 100 g of final product | | Amount |
|---|---|---|
| Thiazolidinedione | Rosiglitazone | 1 g |
| Antioxidant | alpha-Tocopherol | 0.002 g |
| Percutaneous carrier | Ethanol, anhydrous | 69 g |
| | Propylene glycol | 27 g |
| | Oleic acid | 3 g |
| Viscosity enhancing agent | Hdroxypropylcellulose (e.g., Klucel ® Grade HF) | 1 g |

Rosiglitazone was dissolved in ethanol. Propylene glycol and oleic acid were added, and the resulting preparation was thoroughly mixed. Hydroxypropylcellulose was added and thoroughly mixed to yield about 100 grams of gel with a final rosiglitazone concentration of about 1% (w/w).

Example 4

Figure 5:
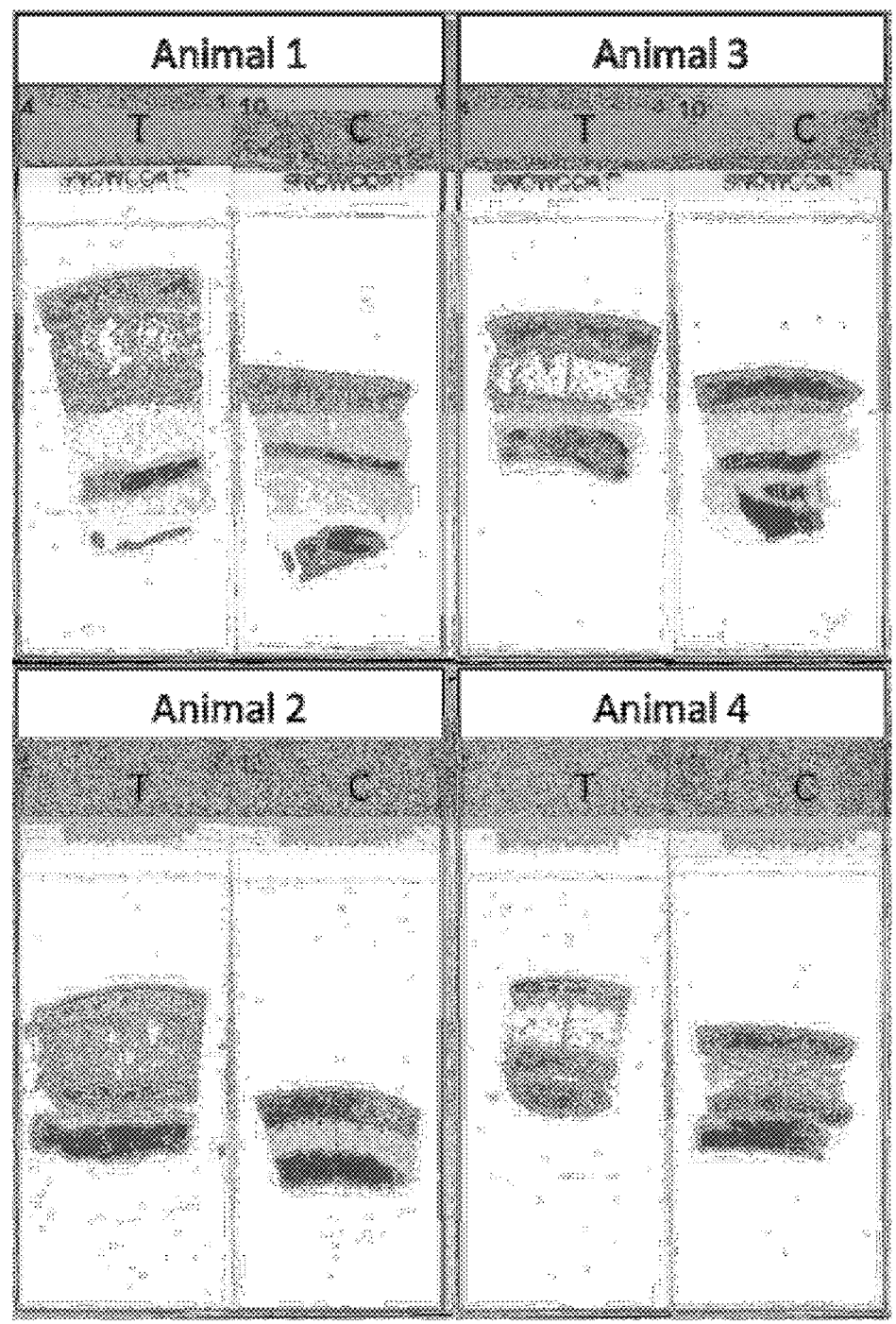
FIG. 5 shows representative low-power views of hematoxylin- and eosin-stained axial sections of tissue from the right and left flanks of minipigs treated with percutaneous rosiglitazone (slides marked "T") or vehicle (slides marked "C"). Slides pairs are from anatomic sites that are precisely contralateral to one another. See Example 4 for further details. All panels shown at same magnification.

A prospective controlled trial was performed in 4 Gottingen minipigs (2 males, 2 females). Hair on the back was clipped. A square-shaped Rosiglitazone Treatment Area (50 $cm^2$) was marked on the right side of each animal. An equivalent Vehicle Treatment Area was marked on the left side of the animal, such that the two treatment areas were anatomically equivalent. Each Rosiglitazone Treatment Area was treated once daily with 0.3 mL of the composition of Example 3; each Vehicle Treatment Area was treated once daily with 0.3 mL of a corresponding vehicle (no rosiglitazone). Animals were fed a standard diet, and observed for skin condition and overall health. After 42 days of treatment, plasma pharmacokinetics (PK) was assessed on all animals by Liquid Chromatography/Tandem Mass Spectrometry. Necropsy was done and samples of skin, subcutaneous fat, and muscle were collected en bloc from each treatment area in a controlled fashion. Samples were fixed in formalin, stained with hematoxylin and eosin, examined microscopically, and measured digitally at 6 systematically controlled locations per treatment area (each location precisely contralateral to its counterpart on the opposite treatment area). The treatment was well tolerated, with no evidence of skin irritation or other clinical observations. FIG. 5 shows representative histologic results (skin at top of each slide; vertical line indicates distance from deep surface of dermis to panniculus carnosus, which is a muscle landmark). Increased thickness of the subcutaneous fat is apparent on treated tissue (T) compared to the respective control (C). Table 5 presents the thicknesses of subcutaneous fat on each of six treated and control (vehicle) locations, by animal. Treatment with percutaneous rosiglitazone was associated with a statistically significant, 48% local increase in subcutaneous fat thickness (p<0.0001). Table 6 compares plasma PK following percutaneous administration (present study) with plasma PK following oral administration in humans. Peak plasma concentrations and exposure following percutaneous administration were negligible, i.e., about 3400- and 1300-fold lower than for oral (systemic) therapy. Thus, in a large mammal with skin similar to that of a human, daily administration of rosiglitazone in a working percutaneous formulation caused local increases in subcutaneous fat without any apparent systemic effect. Furthermore, systemic drug levels were pharmacologically negligible.

TABLE 5

| Location | Animal | Fat Thickness (mm) | | Rosiglizazone |
| | | Rosiglitazone | Vehicle | Increase over Placebo |
| --- | --- | --- | --- | --- |
| A | 1 | 7.87 | 6.13 | 28% |
| A | 2 | 5.09 | 2.55 | 100% |
| A | 3 | 7.30 | 5.10 | 43% |
| A | 4 | 5.72 | 5.28 | 8% |
| B | 1 | 7.82 | 4.58 | 71% |
| B | 2 | 7.47 | 3.57 | 110% |
| B | 3 | 6.47 | 5.26 | 23% |
| B | 4 | 5.86 | 4.25 | 38% |
| C | 1 | 9.84 | 5.65 | 74% |
| C | 2 | 6.47 | 3.16 | 104% |
| C | 3 | 8.62 | 5.66 | 52% |
| C | 4 | 3.95 | 5.16 | −23% |
| D | 1 | 7.24 | 6.33 | 14% |
| D | 2 | 5.20 | 3.62 | 44% |
| D | 3 | 7.68 | 3.97 | 94% |
| D | 4 | 3.73 | 4.07 | −8% |
| E | 1 | 5.59 | 4.54 | 23% |
| E | 2 | 3.70 | 1.86 | 99% |
| E | 3 | 8.46 | 4.82 | 76% |
| E | 4 | 4.21 | 4.66 | −10% |
| F | 1 | 6.39 | 4.40 | 45% |
| F | 2 | 3.07 | 1.85 | 66% |
| F | 3 | 8.30 | 5.21 | 59% |
| F | 4 | 4.88 | 3.72 | 31% |
| MEAN | | 6.29* | 4.39 | 48% | p < .0001 (paired t-test)

TABLE 6

| Parameter | Percutaneous | Oral** | Percutaneous:Oral Ratio |
| --- | --- | --- | --- |
| Absolute Dose mg/d | 3 | 4 | 0.75 |
| Peak plasma level ($C_{max}$) ng/mL | 0.1* | 355 | ~3400 |
| Plasma exposure ($AUC_{0-24}$) ng * h/mL | 1.9* | 2542 | ~1300 |

$AUC_{0-24}$ = Area Under the Curve, 0-24 hours
*Human equivalent (mean pig weight 14 kg, human scaling factor = 5)
**Chen et al., Simultaneous determination and pharmacokinetic study of metformin and rosiglitazone in human plasma by HPLC-ESI-MS, J Chromatog Sci (2011) 49: 94-100. Dose is typical dose for adults with diabetes.

Example 5

To identify potential percutaneous formulations, skin permeation studies were conducted with various formulations of rosiglitazone, ex vivo, on fresh minipig skin. Harvested skin was mounted on a standard (Franz-type) diffusion cell apparatus. All test articles contained 0.1% (weight/weight) of rosiglitazone. Each test article (8 mg) was uniformly applied to a skin surface of 0.8 cm$^2$. Treated skin was left open to the atmosphere to simulate clinical conditions. Receptor fluid flowed continuously over 24 hours and was collected in fractions. The amount of rosiglitazone in these fractions was determined by Liquid Chromatography/Tandem Mass Spectrometry. The following amounts of drug were recovered from receptor fluid over 24 hours:

TABLE 7

| Formulation | Drug mass (ng, mean) |
| --- | --- |
| Lipoderm ® | 0 |
| 1,3-butanediol | 0 |
| Ethanol 70%, PG 30% | 770 |
| Ethanol 70%, PG 27%, oleic acid 3% | 3129 |
| Ethanol 75%, LL 25% | 2367 |

LL = lauryl lactate,
PG = propylene glycol

Thus, in a study in ex vivo skin, a formulation of rosiglitazone comprising oleic acid provided superior drug penetration compared to a range of other formulations and known enhancers, including Lipoderm®, butanediol, and lauryl lactate.

Example 6

The following experiment describes a randomized, double-blind study in human subjects to test if a percutaneously administered thiazolidinedione increases fat in the cheeks of HIV-seropositive patients on antiretroviral therapy who are suffering from HIV lipodystrophy.

Eligible subjects (for example, n=40) with HIV lipodystrophy and characteristic facial fat atrophy are entered into a randomized double-blind study. Subjects are randomized in 1:1 fashion to receive either rosiglitazone (for example, 1% in a percutaneous vehicle), or vehicle alone. The vehicle is, for example, according to Example 3. Products are unlabeled as to the presence of rosiglitazone or vehicle. Subjects are instructed to apply, once a day, the contents of one syringe to the cheeks.

Serial clinical exams and non-invasive imaging are conducted at the beginning of the study and then at monthly intervals. Based on clinical exams, the degree of fat atrophy is rated on a scale of 1 to 5. Treatment continues for 3 months.

It is contemplated that after a period of time, for example after 3 months of treatment, pioglitazone will be associated with a subjective and/or objective increase in cheek fat, whereas vehicle will not. Serial noninvasive imaging (for example, ultrasound or computed tomography) will confirm an increase in cheek fat due to an increase in subcutaneous fat thickness.

Example 7

The following description exemplifies a clinical application of percutaneous administration of a thiazolidinedione for midface augmentation.

A female or male patient wishes to undergo a midface augmentation procedure but is concerned about the risks of surgery. The physician prescribes a daily application of rosiglitazone (for example, as the composition of Example 3) to the skin of both breasts.

It is contemplated that after a period of time, for example after 3 months of treatment, the breasts appear clinically larger. Serial noninvasive imaging (for example, ultrasound or computed tomography) will confirm an increase in breast size due to an increase in subcutaneous fat thickness.

Example 8

The following description exemplifies a clinical application of percutaneous administration of a thiazolidinedione for breast augmentation.

A female or male patient wishes to undergo a breast augmentation procedure but is concerned about the risks of surgery. The physician prescribes a daily application of rosiglitazone (for example, as the composition of Example 3) to the skin of both breasts.

It is contemplated that after a period of time, for example after 3 months of treatment, the breasts appear clinically larger. Serial noninvasive imaging (for example, ultrasound or computed tomography) will confirm an increase in breast size due to an increase in subcutaneous fat thickness.

Example 9

The following description exemplifies a clinical application of percutaneous administration of an orexigenic pregnane derivative for augmentation of the buttocks.

A female or male patient wishes to undergo a buttocks augmentation procedure but is concerned about the risks of surgery. The physician prescribes a daily application of megestrol acetate (for example, 10 mg/ml in Lipoderm®) to the buttocks.

It is contemplated that after a period of time, for example after 6 months of treatment, the buttocks appear clinically larger. Serial noninvasive imaging (for example, ultrasound or computed tomography) will confirm an increase in buttocks size due to an increase in subcutaneous fat thickness.

Example 10

The following description exemplifies application of the invention to reduce skin wrinkles.

A female or male patient is bothered by wrinkles on the skin of the hands. The physician prescribes a daily application of rosiglitazone (for example, as the composition of Example 3) to the dorsal skin of both hands.

It is contemplated that after a period of time, for example after 3 months of treatment, the skin wrinkles appear lessened on clinical exam. Serial noninvasive imaging (for example, ultrasound) will confirm an increase in subcutaneous fat thickness on the dorsum of the hands.

Example 11

A study is conducted according to the protocol of Example 4. Concentrations of rosiglitazone are determined in plasma and in fat from the Rosiglitazone Treatment Area and Vehicle Treatment Area (each on a weight per weight basis). It is predicted that rosiglitazone concentrations will be substantially higher in fat from the Rosiglitazone Treatment Area compared to fat from the Vehicle Treatment Area or compared to plasma. For example, it is predicted that rosiglitazone concentrations in fat from the Rosiglitazone Treatment Area will be at least 100-fold, or at least 1000-fold higher than in fat from the Vehicle Treatment Area. Also for example, it is predicted that rosiglitazone concentrations in fat from the Rosiglitazone Treatment Area will be at least 100-fold or at least 1000-fold higher than in plasma.

Other Embodiments

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

What is claimed is:

1. A method for increasing subcutaneous fat locally in a body of a subject in need thereof, the method comprising topically administering to the skin of the subject a thiazolidinedione selected from the group consisting of:

rosiglitazone

pioglitazone

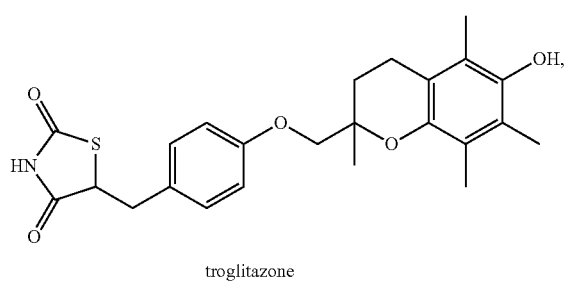

troglitazone

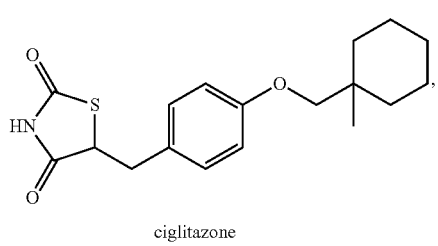

ciglitazone

-continued

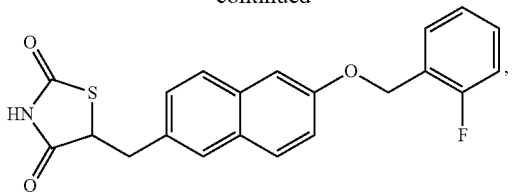

netoglitazone

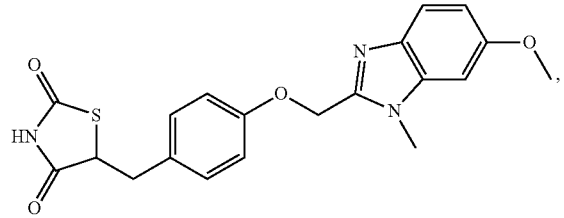

rivoglitazone and pharmaceutically acceptable salts thereof, using a percutaneous carrier selected from the group consisting of ethanol, propylene glycol, oleic acid, and lauryl lactate, in order to deliver an effective amount of the thiazolidinedione to the subcutaneous fat of the subject.

2. The method of claim 1, wherein the subject suffers from a subcutaneous fat deficiency.

3. The method of claim 2, wherein the subcutaneous fat deficiency is associated with a metabolic disorder.

4. The method of claim 2, wherein the subcutaneous fat deficiency is acquired.

5. The method of claim 4, wherein the acquired subcutaneous fat deficiency is HIV-associated lipodystrophy, lipidema, acquired partial lipodystrophy, acquired generalized lipodystrophy, Parry-Romberg syndrome, juvenile dermatomyositis, centrifugal abdominal lipodystrophy, lipoatrophia annularis, or localized lipodystrophy.

6. The method of claim 2, wherein the subcutaneous fat deficiency is caused by a medication, surgery, or an injury.

7. The method of claim 1, wherein the subject suffers from wrinkles of the skin.

8. The method of claim 1, wherein the subject suffers from dissatisfaction with the size or contour of a body part.

9. The method of claim 8, wherein the body part is the face, forehead, periorbital region of the face, cheeks, chin, lips, breast, limbs, hands, trunk, hips, or buttocks.

10. The method of claim 1, wherein the subject has transplanted fat.

11. The method of claim 1, wherein the thiazolidinedione is rosiglitazone or a pharmaceutically acceptable salt thereof.

12. The method of claim 11, wherein the rosiglitazone is administered in a composition at a concentration between about 0.1 percent and about 2 percent by weight.

13. The method of claim 1, wherein the percutaneous carrier comprises oleic acid.

14. The method of claim 13, wherein the oleic acid is administered in a composition at a concentration between about 1 percent and about 5 percent by weight.

15. The method of claim 1, wherein the percutaneous carrier comprises propylene glycol.

16. The method of claim 15, wherein the propylene glycol is administered in a composition at a concentration between about 20 percent and about 40 percent by weight.

17. The method of claim 1, wherein the percutaneous carrier comprises propylene glycol and oleic acid.

18. The method of claim 1, wherein the fat is locally increased by at least 10 percent, at least 20 percent, at least 30 percent, or at least 40 percent compared to control.

19. The method of claim 1, wherein increasing fat locally occurs locally on the face, breast, limbs, hands, trunk, hips, or buttocks.

20. The method of claim 1, wherein the administering is three times a day, twice a day, once a day, every other day, or every third day.

\* \* \* \* \*